US011225647B2

(12) United States Patent
Boer et al.

(10) Patent No.: US 11,225,647 B2
(45) Date of Patent: Jan. 18, 2022

(54) GERANYLGERANYL PYROPHOSPHATE SYNTHASES

(71) Applicant: DSM IP ASSETS B.V., Heerlen (NL)

(72) Inventors: Viktor Marius Boer, Echt (NL); Priscilla Zwartjens, Echt (NL); Johannes Gustaaf Ernst Van Leeuwen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 277 days.

(21) Appl. No.: 16/345,129

(22) PCT Filed: Oct. 26, 2017

(86) PCT No.: PCT/EP2017/077439
§ 371 (c)(1),
(2) Date: Apr. 25, 2019

(87) PCT Pub. No.: WO2018/078014
PCT Pub. Date: May 3, 2018

(65) Prior Publication Data
US 2019/0284539 A1 Sep. 19, 2019

(30) Foreign Application Priority Data
Oct. 27, 2016 (EP) .................................. 16196095

(51) Int. Cl.
| C12N 9/10 | (2006.01) |
| C12N 9/02 | (2006.01) |
| C12N 9/88 | (2006.01) |
| C12P 15/00 | (2006.01) |
| C12P 19/56 | (2006.01) |
| C12N 15/52 | (2006.01) |
| C12P 7/42 | (2006.01) |

(52) U.S. Cl.
CPC .......... *C12N 9/1085* (2013.01); *C12N 9/0073* (2013.01); *C12N 9/88* (2013.01); *C12N 15/52* (2013.01); *C12P 7/42* (2013.01); *C12P 15/00* (2013.01); *C12P 19/56* (2013.01); *C12Y 114/13078* (2013.01); *C12Y 205/01001* (2013.01); *C12Y 402/03019* (2013.01)

(58) Field of Classification Search
None
See application file for complete search history.

(56) References Cited

U.S. PATENT DOCUMENTS

| 6,995,003 | B1 | 2/2006 | Nieboer et al. |
| 7,851,199 | B2 * | 12/2010 | Bailey ................... A61P 3/00 435/254.2 |
| 9,518,188 | B2 | 12/2016 | Lettow et al. |
| 2006/0127972 | A1 | 6/2006 | Nieboer et al. |
| 2010/0192985 | A1 * | 8/2010 | Aehle ..................... C12N 9/50 134/26 |
| 2014/0303036 | A1 | 10/2014 | Roubos et al. |
| 2015/0031868 | A1 | 1/2015 | Lehmann et al. |
| 2016/0153017 | A1 | 6/2016 | Van Der Hoeven et al. |
| 2016/0160257 | A1 | 6/2016 | Broers et al. |
| 2018/0132515 | A1 | 5/2018 | Lawrence et al. |
| 2018/0148697 | A1 | 5/2018 | Royer et al. |
| 2020/0332322 | A1 * | 10/2020 | Kim ........................ C12P 13/12 |

FOREIGN PATENT DOCUMENTS

| EP | 0635574 A | 1/1995 |
| EP | 1499708 B1 | 1/2006 |
| WO | 98/46772 A2 | 10/1998 |
| WO | 99/60102 A2 | 11/1999 |
| WO | 00/37671 A2 | 6/2000 |
| WO | 03/062430 A1 | 7/2003 |
| WO | 04/099381 A2 | 11/2004 |
| WO | 06/009434 A1 | 1/2006 |
| WO | 2006/096130 A1 | 9/2006 |
| WO | 2011/060057 A1 | 5/2011 |
| WO | 2011/123567 A1 | 10/2011 |
| WO | 2013/076280 A1 | 5/2013 |
| WO | 2013/110673 A1 | 8/2013 |
| WO | 2014/122227 A2 | 8/2014 |
| WO | 2015/007748 A1 | 1/2015 |

(Continued)

OTHER PUBLICATIONS

Singh et al., Curr. Protein Pept. Sci. 18:1-11, 2017 (Year: 2017).*
Zhang et al., Structure 26:1474-1485, 2018 (Year: 2018).*
Database UniProt [Online] dated Oct. 14, 2015, retrieved from EBI accession No. UNIPROT: A0A0J9X7P9.
International Search Report of International Patent Application No. PCT/EP2017/077439 dated Jan. 10, 2018.
Humphrey, Tania V. et al., "Spatial organisation of four enzymes from Stevia rebaudiana that are involved in steviol glycoside synthesis", Plant Molecular Biology, 2006, pp. 47-62, vol. 61.

(Continued)

*Primary Examiner* — David Steadman
(74) *Attorney, Agent, or Firm* — McBee Moore & Vanik IP, LLC; Susan McBee; Chester Moore

(57) ABSTRACT

The present invention relates a variant polypeptide having geranylgeranyl pyrophosphate synthase activity, which variant polypeptide comprises an amino acid sequence which, when aligned with a geranylgeranyl pyrophosphate synthase comprising the sequence set out in SEQ ID NO: 1, comprises at least one substitution of an amino acid residue corresponding to any of amino acids at positions 92, 100 or 235 said positions being defined with reference to SEQ ID NO: 1 and wherein the variant has one or more modified properties as compared with a reference polypeptide having geranylgeranyl pyrophosphate synthase activity. A variant polypeptide of the invention may be used in a recombinant host for the production of steviol or a steviol glycoside.

7 Claims, 1 Drawing Sheet
Specification includes a Sequence Listing.

(56) References Cited

FOREIGN PATENT DOCUMENTS

WO      2015/011209 A1      1/2015
WO      2016/170045 A1      10/2016

OTHER PUBLICATIONS

Mohamed, Amal A.A. et al., "UDP-dependent glycosyltransferases involved in the biosynthesis of steviol glycosides", Journal of Plant Physiology, 2011, pp. 1136-1141, vol. 168.

Shirley, Renee L. et al., "Nuclear Import of Upf3p Is Mediated by Importing-[alpha]/-[beta] and Export to the Cytoplasm Is Required for a Functional Nonsense-Mediated mRNA Decay Pathway in Yeast", Genetics, Aug. 2002, pp. 1465-1482, vol. 161.

Fierro, Francisco et al., "Autonomously replicating plasmids carrying the AMA1 region in Penicillium chrysogenum", Current Genetics, 1996, pp. 482-489, vol. 29.

Fleer, R. et al., "Stable Multicopy Vectors for High-Level Secretion of Recombinant Human Serum Albumin by Kluyveromyces Yeasts", Bio/Technology, Oct. 1991, pp. 968-975, vol. 9.

\* cited by examiner

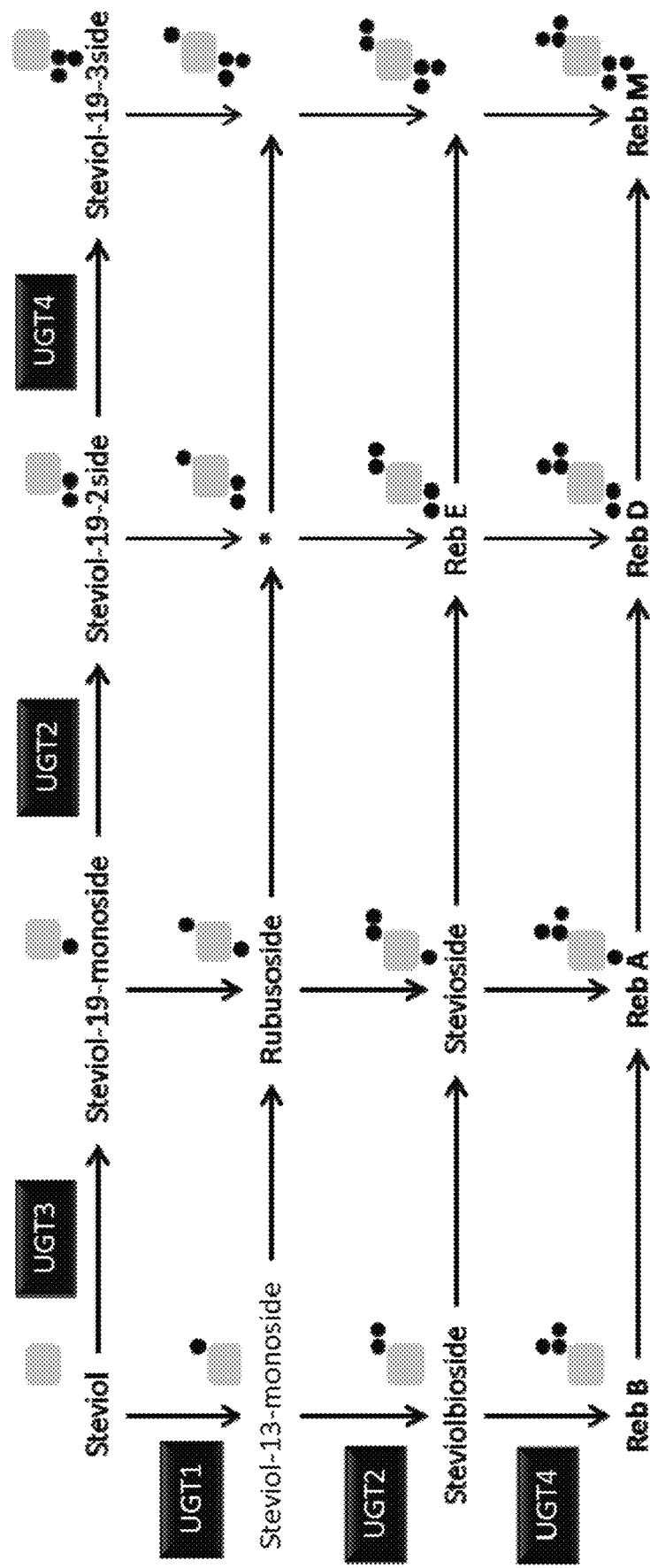

```
                       SEQUENCE LISTING

<160> NUMBER OF SEQ ID NOS: 33

<210> SEQ ID NO 1
<211> LENGTH: 327
<212> TYPE: PRT
<213> ORGANISM: Yarrowia lipolytica

<400> SEQUENCE: 1

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
    50                  55                  60

His Asn Ser Ser Leu Leu Val Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
    130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
    210                 215                 220
```

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
            245                 250                 255

Ser Leu Lys Lys Tyr Ala Val Asp Tyr Met Arg Thr Glu Thr Lys Ser
        260                 265                 270

Phe Asp Tyr Cys Leu Lys Arg Ile Gln Ala Met Ser Leu Lys Ala Ser
    275                 280                 285

Ser Tyr Ile Asp Asp Leu Ala Ala Gly His Asp Val Ser Lys Leu
        290                 295                 300

Arg Ala Ile Leu His Tyr Phe Val Ser Thr Ser Asp Cys Glu Glu Arg
305                 310                 315                 320

Lys Tyr Phe Glu Asp Ala Gln
            325

<210> SEQ ID NO 2
<211> LENGTH: 984
<212> TYPE: DNA
<213> ORGANISM: Yarrowia lipolytica

<400> SEQUENCE: 2
atggattata acagcgcgga tttcaaggag atctggggca aggccgccga caccgcgctg      60
ctgggaccgt acaactacct cgccaacaac cggggccaca acatcagaga acacttgatc    120
gcagcgttcg gagcggttat caaggtggac aagagcgatc tcgaaaccat ttcgcacatc    180
accaagattt tgcataactc gtcgctgctt gttgatgacg tggaagacaa ctcgatgctc    240
cgacgaggcc tgccggcagc ccattgtctg ttttggagtcc cccaaaccat caactccgcc    300
aactacatgt actttgtggc tctgcaggag gtgctcaagc tcaagtctta tgatgccgtc    360
tccattttca ccgaggaaat gatcaacttg catagaggtc agggtatgga tctctactgg    420
agagaaacac tcacttgccc ctcggaagac gagtatctgg agatggtggt gcacaagacc    480
ggaggactgt ttcggctggc tctgagactt atgctgtcgg tggcatcgaa acaggaggac    540
catgaaaaga tcaactttga tctcacacac cttaccgaca cactgggagt catttaccag    600
attctggatg attacctcaa cctgcagtcc acggaattga ccgagaacaa gggattctgc    660
gaagatatca gcgaaggaaa gttttcgttt ccgctgattc acagcatccg gaccaacccg    720
gataaccacg agattctcaa cattctcaaa cagcgaacaa gcgacgcttc actcaaaaag    780
tacgccgtgg actacatgag aacagaaacc aagagtttcg actactgcct caagagaatc    840
caggccatgt cactcaaggc aagttcgtac attgatgatc tcgcagcagc cggccacgat    900
gtctccaagt tgcgagccat tttgcattat tttgtgtcca cctctgactg tgaggagaga    960
aagtactttg aggatgcgca gtaa                                            984

<210> SEQ ID NO 3
<211> LENGTH: 327
<212> TYPE: PRT
<213> ORGANISM: Artificial sequence
<220> FEATURE:
<223> OTHER INFORMATION: GGS variant

<400> SEQUENCE: 3

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
 35                  40                  45

Val Asp Lys Ser Asp Leu Glu Thr Ile Ser His Ile Thr Lys Ile Leu
 50                  55                  60

His Asn Ser Ser Leu Leu Val Asp Asp Val Glu Asp Asn Ser Met Leu
 65                  70                  75                  80

Arg Arg Gly Leu Pro Ala Ala His Cys Leu Phe Glu Val Pro Gln Thr
                 85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
            115                 120                 125

Asn Leu His Arg Gly Gln Gly Met Asp Leu Tyr Trp Arg Glu Thr Leu
130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
            195                 200                 205

Gln Ser Thr Glu Leu Thr Glu Asn Lys Gly Phe Cys Glu Asp Ile Ser
210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
            275                 280                 285

Ser Tyr Ile Asp Asp Leu Ala Ala Ala Gly His Asp Val Ser Lys Leu
290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 4
<211> LENGTH: 984
<212> TYPE: DNA
<213> ORGANISM: Artificial sequence
<220> FEATURE:
<223> OTHER INFORMATION: Coding sequence for variant GGS

<400> SEQUENCE: 4
atggattata acagcgcgga tttcaaggag atctggggca aggccgccga caccgcgctg      60
ctgggaccgt acaactacct cgccaacaac cggggccaca acatcagaga acacttgatc     120
gcagcgttcg gagcggttat caaggtggac aagagcgatc tcgaaaccat ttcgcacatc     180
accaagattt tgcataactc gtcgctgctt gttgatgacg tggaagacaa ctcgatgctc     240
cgacgaggcc tgccggcagc ccattgtctg tttgaagtcc cccaaaccat caactccgcc     300
aactacatgt actttgtggc tctgcaggag gtgctcaagc tcaagtctta tgatgccgtc     360

```
tccattttca ccgaggaaat gatcaacttg catagaggtc agggtatgga tctctactgg    420
agagaaacac tcacttgccc ctcggaagac gagtatctgg agatggtggt gcacaagacc    480
ggaggactgt ttcggctggc tctgagactt atgctgtcgg tggcatcgaa acaggaggac    540
catgaaaaga tcaactttga tctcacacac cttaccgaca cactgggagt catttaccag    600
attctggatg attacctcaa cctgcagtcc acggaattga ccgagaacaa gggattctgc    660
gaagatatca gcgaaggaaa gttttcgttt ccgctgattc acagcatccg gaccaacccg    720
gataaccacg agattctcaa cattctcaaa cagcgaacaa gcgacgcttc actcaaaaag    780
tacgccgtgg actacatgag aacagaaacc aagagtttcg actactgcct caagagaatc    840
caggccatgt cactcaaggc aagttcgtac attgatgatc tcgcagcagc cggccacgat    900
gtctccaagt tgcgagccat tttgcattat tttgtgtcca cctctgactg tgaggagaga    960
aagtactttg aggatgcgca gtaa                                           984
```

<210> SEQ ID NO 5
<211> LENGTH: 327
<212> TYPE: PRT
<213> ORGANISM: Artificial sequence
<220> FEATURE:
<223> OTHER INFORMATION: Variant GGS

<400> SEQUENCE: 5

```
Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
    50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Val Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
    130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
                245                 250                 255
```

```
Ser Leu Lys Lys Tyr Ala Val Asp Tyr Met Arg Thr Glu Thr Lys Ser
        260                 265                 270

Phe Asp Tyr Cys Leu Lys Arg Ile Gln Ala Met Ser Leu Lys Ala Ser
    275                 280                 285

Ser Tyr Ile Asp Asp Leu Ala Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 6
<211> LENGTH: 984
<212> TYPE: DNA
<213> ORGANISM: Artificial sequence
<220> FEATURE:
<223> OTHER INFORMATION: Coding sequence for variant GGS

<400> SEQUENCE: 6
atggattata acagcgcgga tttcaaggag atctggggca aggccgccga caccgcgctg      60
ctgggaccgt acaactacct cgccaacaac cggggccaca acatcagaga acacttgatc    120
gcagcgttcg gagcggttat caaggtggac aagagcgatc tcgaaaccat ttcgcacatc    180
accaagattt tgcataactc gtcgctgctt gttgatgacg tggaagacaa ctcgatgctc    240
cgacgaggcc tgccggcagc ccattgtctg tttggagtcc cccaaaccat caactccgtc    300
aactacatgt actttgtggc tctgcaggag gtgctcaagc tcaagtctta tgatgccgtc    360
tccattttca ccgaggaaat gatcaacttg catagaggtc agggtatgga tctctactgg    420
agagaaacac tcacttgccc ctcggaagac gagtatctgg agatggtggt gcacaagacc    480
ggaggactgt ttcggctggc tctgagactt atgctgtcgg tggcatcgaa acaggaggac    540
catgaaaaga tcaactttga tctcacacac cttaccgaca cactgggagt catttaccag    600
attctggatg attacctcaa cctgcagtcc acggaattga ccgagaacaa gggattctgc    660
gaagatatca gcgaaggaaa gttttcgttt ccgctgattc acagcatccg gaccaacccg    720
gataaccacg agattctcaa cattctcaaa cagcgaacaa gcgacgcttc actcaaaaag    780
tacgccgtgg actacatgag aacagaaacc aagagtttcg actactgcct caagagaatc    840
caggccatgt cactcaaggc aagttcgtac attgatgatc tcgcagcagc cggccacgat    900
gtctccaagt tgcgagccat tttgcattat tttgtgtcca cctctgactg tgaggagaga    960
aagtactttg aggatgcgca gtaa                                           984

<210> SEQ ID NO 7
<211> LENGTH: 327
<212> TYPE: PRT
<213> ORGANISM: Artificial sequence
<220> FEATURE:
<223> OTHER INFORMATION: Variant GGS

<400> SEQUENCE: 7

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45
```

Val Asp Lys Ser Asp Leu Glu Thr Ile Ser His Ile Thr Lys Ile Leu
         50                  55                  60

His Asn Ser Ser Leu Leu Val Asp Asp Val Glu Asp Asn Ser Met Leu
 65                  70                  75                  80

Arg Arg Gly Leu Pro Ala Ala His Cys Leu Phe Gly Val Pro Gln Thr
                 85                  90                  95

Ile Asn Ser Ala Asn Tyr Met Tyr Phe Val Ala Leu Gln Glu Val Leu
                100                 105                 110

Lys Leu Lys Ser Tyr Asp Ala Val Ser Ile Phe Thr Glu Glu Met Ile
            115                 120                 125

Asn Leu His Arg Gly Gln Gly Met Asp Leu Tyr Trp Arg Glu Thr Leu
130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
                180                 185                 190

Asp Thr Leu Gly Val Ile Tyr Gln Ile Leu Asp Asp Tyr Leu Asn Leu
            195                 200                 205

Gln Ser Thr Glu Leu Thr Glu Asn Lys Gly Phe Cys Glu Asp Ile Ser
210                 215                 220

Glu Gly Lys Phe Ser Phe Pro Leu Ile His Asn Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
                260                 265                 270

Phe Asp Tyr Cys Leu Lys Arg Ile Gln Ala Met Ser Leu Lys Ala Ser
            275                 280                 285

Ser Tyr Ile Asp Asp Leu Ala Ala Ala Gly His Asp Val Ser Lys Leu
290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 8
<211> LENGTH: 984
<212> TYPE: DNA
<213> ORGANISM: Artificial sequence
<220> FEATURE:
<223> OTHER INFORMATION: Coding sequence for GGS

<400> SEQUENCE: 8
atggattata  tcagcgcgga  tttcaaggag  atctggggca  aggccgccga  caccgcgctg      60
ctgggaccgt  acaactacct  cgccaacaac  cggggccaca  acatcagaga  acacttgatc     120
gcagcgttcg  gagcggttat  caaggtggac  aagagcgatc  tcgaaaccat  ttcgcacatc     180
accaagattt  tgcataactc  gtcgctgctt  gttgatgacg  tggaagacaa  ctcgatgctc     240
cgacgaggcc  tgccggcagc  ccattgtctg  tttggagtcc  cccaaaccat  caactccgcc     300
aactacatgt  actttgtggc  tctgcaggag  gtgctcaagc  tcaagtctta  tgatgccgtc     360
tccattttca  ccgaggaaat  gatcaacttg  catagaggtc  agggtatgga  tctctactgg     420
agagaaacac  tcacttgccc  ctcggaagac  gagtatctgg  agatggtggt  gcacaagacc     480

```
ggaggactgt tccggctggc tctgagactt atgctgtcgg tggcatcgaa acaggaggac    540
catgaaaaga tcaactttga tctcacacac cttaccgaca cactgggagt catttaccag    600
attctggatg attacctcaa cctgcagtcc acggaattga ccgagaacaa gggattctgc    660
gaagatatca gcgaaggaaa gttttcgttt ccgctgattc acaacatccg gaccaacccg    720
gataaccacg agattctcaa cattctcaaa cagcgaacaa gcgacgcttc actcaaaaag    780
tacgccgtgg actacatgag aacagaaacc aagagtttcg actactgcct caagagaatc    840
caggccatgt cactcaaggc aagttcgtac attgatgatc tcgcagcagc cggccacgat    900
gtctccaagt tgcgagccat tttgcattat tttgtgtcca cctctgactg tgaggagaga    960
aagtactttg aggatgcgca gtaa                                           984
```

<210> SEQ ID NO 9
<211> LENGTH: 327
<212> TYPE: PRT
<213> ORGANISM: Artificial sequence
<220> FEATURE:
<223> OTHER INFORMATION: Variant GGS

<400> SEQUENCE: 9

```
Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
    50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Glu Val Pro Gln Thr
                85                  90                  95

Ile Asn Ser Val Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
    130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270
```

Phe Asp Tyr Cys Leu Lys Arg Ile Gln Ala Met Ser Leu Lys Ala Ser
            275                 280                 285

Ser Tyr Ile Asp Asp Leu Ala Ala Ala Gly His Asp Val Ser Lys Leu
        290                 295                 300

Arg Ala Ile Leu His Tyr Phe Val Ser Thr Ser Asp Cys Glu Glu Arg
305                 310                 315                 320

Lys Tyr Phe Glu Asp Ala Gln
            325

<210> SEQ ID NO 10
<211> LENGTH: 984
<212> TYPE: DNA
<213> ORGANISM: Artificial sequence
<220> FEATURE:
<223> OTHER INFORMATION: Coding sequence for variant GGS

<400> SEQUENCE: 10

```
atggattata acagcgcgga tttcaaggag atctggggca aggccgccga caccgcgctg      60
ctgggaccgt acaactacct cgccaacaac cggggccaca acatcagaga cacttgatc     120
gcagcgttcg gagcggttat caaggtggac aagagcgatc tcgaaaccat ttcgcacatc    180
accaagattt tgcataactc gtcgctgctt gttgatgacg tggaagacaa ctcgatgctc    240
cgacgaggcc tgccggcagc ccattgtctg tttgaagtcc cccaaaccat caactccgtc    300
aactacatgt actttgtggc tctgcaggag gtgctcaagc tcaagtctta tgatgccgtc    360
tccattttca ccgaggaaat gatcaacttg catagaggtc agggtatgga tctctactgg    420
agagaaacac tcacttgccc ctcggaagac gagtatctgg agatggtggt gcacaagacc    480
ggaggactgt tcggctggc tctgagactt atgctgtcgg tggcatcgaa acaggaggac    540
catgaaaaga tcaactttga tctcacacac cttaccgaca cactgggagt catttaccag    600
attctggatg attacctcaa cctgcagtcc acggaattga ccgagaacaa gggattctgc    660
gaagatatca gcgaaggaaa gttttcgttt ccgctgattc acagcatccg gaccaacccg    720
gataaccacg agattctcaa cattctcaaa cagcgaacaa gcgacgcttc actcaaaaag    780
tacgccgtgg actacatgag aacagaaacc aagagtttcg actactgcct caagagaatc    840
caggccatgt cactcaaggc aagttcgtac attgatgatc tcgcagcagc cggccacgat    900
gtctccaagt tgcgagccat tttgcattat tttgtgtcca cctctgactg tgaggagaga    960
aagtactttg aggatgcgca gtaa                                           984
```

<210> SEQ ID NO 11
<211> LENGTH: 327
<212> TYPE: PRT
<213> ORGANISM: Artificial sequence
<220> FEATURE:
<223> OTHER INFORMATION: Variant GGS

<400> SEQUENCE: 11

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
    50                  55                  60

His Asn Ser Ser Leu Leu Val Asp Asp Val Glu Asp Asn Ser Met Leu
 65                  70                  75                  80

Arg Arg Gly Leu Pro Ala Ala His Cys Leu Phe Glu Val Pro Gln Thr
                 85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
    130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Asn Ile Arg Thr Asn Pro
225                 230                 235                 240

Asp Asn His Glu Ile Leu Asn Ile Leu Lys Gln Arg Thr Ser Asp Ala
            245                 250                 255

Ser Leu Lys Lys Tyr Ala Val Asp Tyr Met Arg Thr Glu Thr Lys Ser
        260                 265                 270

Phe Asp Tyr Cys Leu Lys Arg Ile Gln Ala Met Ser Leu Lys Ala Ser
    275                 280                 285

Ser Tyr Ile Asp Asp Leu Ala Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 12
<211> LENGTH: 984
<212> TYPE: DNA
<213> ORGANISM: Artificial sequence
<220> FEATURE:
<223> OTHER INFORMATION: Coding sequence for variant GGS

<400> SEQUENCE: 12
atggattata cagcgcgga tttcaaggag atctggggca aggccgccga caccgcgctg      60
ctgggaccgt acaactacct cgccaacaac cggggccaca acatcagaga cacttgatc    120 gcagcgttcg gagcggttat caaggtggac aagagcgatc tcgaaaccat ttcgcacatc    180
accaagattt tgcataactc gtcgctgctt gttgatgacg tggaagacaa ctcgatgctc    240
cgacgaggcc tgccggcagc ccattgtctg tttgaagtcc cccaaaccat caactccgcc    300
aactacatgt actttgtggc tctgcaggag gtgctcaagc tcaagtctta tgatgccgtc    360
tccattttca ccgaggaaat gatcaacttg catagaggtc agggtatgga tctctactgg    420
agagaaacac tcacttgccc ctcggaagac gagtatctgg agatggtggt gcacaagacc    480
ggaggactgt ttcggctggc tctgagactt atgctgtcgg tggcatcgaa acaggaggac    540

-continued

```
catgaaaaga tcaactttga tctcacacac cttaccgaca cactgggagt catttaccag    600
attctggatg attacctcaa cctgcagtcc acggaattga ccgagaacaa gggattctgc    660
gaagatatca gcgaaggaaa gttttcgttt ccgctgattc acaacatccg gaccaacccg    720
gataaccacg agattctcaa cattctcaaa cagcgaacaa gcgacgcttc actcaaaaag    780
tacgccgtgg actacatgag aacagaaacc aagagtttcg actactgcct caagagaatc    840
caggccatgt cactcaaggc aagttcgtac attgatgatc tcgcagcagc cggccacgat    900
gtctccaagt tgcgagccat tttgcattat tttgtgtcca cctctgactg tgaggagaga    960
aagtactttg aggatgcgca gtaa                                           984
```

```
<210> SEQ ID NO 13
<211> LENGTH: 327
<212> TYPE: PRT
<213> ORGANISM: Artificial sequence
<220> FEATURE:
<223> OTHER INFORMATION: Variant GGS

<400> SEQUENCE: 13
```

```
Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
    50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Val Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
    130                 135                 140

Thr Cys Pro Ser Glu Asp Glu Tyr Leu Glu Met Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Asn Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285
```

Ser Tyr Ile Asp Asp Leu Ala Ala Gly His Asp Val Ser Lys Leu
        290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 14
<211> LENGTH: 984
<212> TYPE: DNA
<213> ORGANISM: Artificial sequence
<220> FEATURE:
<223> OTHER INFORMATION: Coding sequence for GGS

<400> SEQUENCE: 14
atggattata acagcgcgga tttcaaggag atctggggca aggccgccga caccgcgctg      60
ctgggaccgt acaactacct cgccaacaac cggggccaca acatcagaga acacttgatc     120
gcagcgttcg gagcggttat caaggtggac aagagcgatc tcgaaaccat ttcgcacatc     180
accaagattt tgcataactc gtcgctgctt gttgatgacg tggaagacaa ctcgatgctc     240
cgacgaggcc tgccggcagc ccattgtctg tttggagtcc cccaaaccat caactccgtc     300
aactacatgt actttgtggc tctgcaggag gtgctcaagc tcaagtctta tgatgccgtc     360
tccattttca ccgaggaaat gatcaacttg catagaggtc agggtatgga tctctactgg     420
agagaaacac tcacttgccc ctcggaagac gagtatctgg agatggtggt gcacaagacc     480
ggaggactgt ttcggctggc tctgagactt atgctgtcgg tggcatcgaa acaggaggac     540
catgaaaaga tcaactttga tctcacacac cttaccgaca cactgggagt catttaccag     600
attctggatg attacctcaa cctgcagtcc acggaattga ccgagaacaa gggattctgc     660
gaagatatca gcgaaggaaa gttttcgttt ccgctgattc acaacatccg gaccaacccg     720
gataaccacg agattctcaa cattctcaaa cagcgaacaa gcgacgcttc actcaaaaag     780
tacgccgtgg actacatgag aacagaaacc aagagtttcg actactgcct caagagaatc     840
caggccatgt cactcaaggc aagttcgtac attgatgatc tcgcagcagc cggccacgat     900
gtctccaagt tgcgagccat tttgcattat tttgtgtcca cctctgactg tgaggagaga     960
aagtactttg aggatgcgca gtaa                                            984

<210> SEQ ID NO 15
<211> LENGTH: 327
<212> TYPE: PRT
<213> ORGANISM: Artificial sequence
<220> FEATURE:
<223> OTHER INFORMATION: Variant GGS

<400> SEQUENCE: 15

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
                20                  25                  30

His Asn Ile Arg Glu His Leu Ile Ala Ala Phe Gly Ala Val Ile Lys
            35                  40                  45

Val Asp Lys Ser Asp Leu Glu Thr Ile Ser His Ile Thr Lys Ile Leu
        50                  55                  60

His Asn Ser Ser Leu Leu Val Asp Asp Val Glu Asp Asn Ser Met Leu
65                  70                  75                  80

```
Arg Arg Gly Leu Pro Ala Ala His Cys Leu Phe Glu Val Pro Gln Thr
                85                  90                  95

Ile Asn Ser Val Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
    130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Asn Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 16
<211> LENGTH: 984
<212> TYPE: DNA
<213> ORGANISM: Artificial sequence
<220> FEATURE:
<223> OTHER INFORMATION: Coding sequence for variant GGS

<400> SEQUENCE: 16
atggattata cagcgcgga tttcaaggag atctggggca aggccgccga caccgcgctg      60
ctgggaccgt acaactacct cgccaacaac cggggccaca acatcagaga cacttgatc     120 gcagcgttcg gagcggttat caaggtggac aagagcgatc tcgaaaccat ttcgcacatc    180
accaagattt tgcataactc gtcgctgctt gttgatgacg tggaagacaa ctcgatgctc    240
cgacgaggcc tgccggcagc ccattgtctg tttgaagtcc cccaaaccat caactccgtc    300
aactacatgt actttgtggc tctgcaggag gtgctcaagc tcaagtctta tgatgccgtc    360
tccattttca ccgaggaaat gatcaacttg catagaggtc agggtatgga tctctactgg    420
agagaaacac tcacttgccc ctcggaagac gagtatctgg atggtggt gcacaagacc      480 ggaggactgt tcggctggc tctgagactt atgctgtcgg tggcatcgaa acaggaggac     540
catgaaaaga tcaactttga tctcacacac cttaccgaca cactgggagt catttaccag    600
attctggatg attaccctcaa cctgcagtcc acggaattga ccgagaacaa gggattctgc    660
```

```
gaagatatca gcgaaggaaa gttttcgttt ccgctgattc acaacatccg gaccaacccg    720
gataaccacg agattctcaa cattctcaaa cagcgaacaa gcgacgcttc actcaaaaag    780
tacgccgtgg actacatgag aacagaaacc aagagtttcg actactgcct caagagaatc    840
caggccatgt cactcaaggc aagttcgtac attgatgatc tcgcagcagc cggccacgat    900
gtctccaagt tgcgagccat tttgcattat tttgtgtcca cctctgactg tgaggagaga    960
aagtactttg aggatgcgca gtaa                                            984
```

<210> SEQ ID NO 17
<211> LENGTH: 303
<212> TYPE: PRT
<213> ORGANISM: Mucor circinelloides

<400> SEQUENCE: 17

```
Met Leu Asn Ser His Asn Arg Thr Glu Glu Arg Ser Thr Glu Asp Ile
1               5                   10                  15

Ile Leu Glu Pro Tyr Thr Tyr Leu Ile Ser Gln Pro Gly Lys Asp Ile
            20                  25                  30

Arg Ala Lys Leu Ile Ser Ala Phe Asp Leu Trp Leu His Val Pro Lys
        35                  40                  45

Asp Val Leu Cys Val Ile Asn Lys Ile Ile Gly Met Leu His Asn Ala
    50                  55                  60

Ser Leu Met Ile Asp Asp Val Gln Asp Ser Asp Leu Arg Arg Gly
65                  70                  75                  80

Val Pro Val Ala His His Ile Tyr Gly Val Pro Gln Thr Ile Asn Thr
                85                  90                  95

Ala Asn Tyr Val Ile Phe Leu Ala Leu Gln Glu Val Met Lys Leu Asn
            100                 105                 110

Ile Pro Ser Met Met Gln Val Cys Thr Glu Glu Leu Ile Asn Leu His
        115                 120                 125

Arg Gly Gln Gly Ile Glu Leu Tyr Trp Arg Asp Ser Leu Thr Cys Pro
    130                 135                 140

Thr Glu Glu Glu Tyr Ile Asp Met Val Asn Asn Lys Thr Ser Gly Leu
145                 150                 155                 160

Leu Arg Leu Ala Val Arg Leu Met Gln Ala Ala Ser Glu Ser Asp Ile
                165                 170                 175

Asp Tyr Thr Pro Leu Val Asn Ile Ile Gly Ile His Phe Gln Val Arg
            180                 185                 190

Asp Asp Tyr Met Asn Leu Gln Ser Thr Ser Tyr Thr Asn Asn Lys Gly
        195                 200                 205

Phe Cys Glu Asp Leu Thr Glu Gly Lys Phe Ser Phe Pro Ile Ile His
    210                 215                 220

Ala Ile Arg Lys Asp Pro Ser Asn Arg Gln Leu Leu Asn Ile Ile Ser
225                 230                 235                 240

Gln Lys Pro Thr Ser Ile Glu Val Lys Lys Tyr Ala Leu Glu Val Ile
                245                 250                 255

Arg Lys Ala Gly Ser Phe Glu Tyr Val Arg Glu Phe Leu Arg Gln Lys
            260                 265                 270

Glu Ala Glu Ser Leu Lys Glu Ile Lys Arg Leu Gly Gly Asn Pro Leu
        275                 280                 285

Leu Glu Lys Tyr Ile Glu Thr Ile Arg Val Glu Ala Thr Asn Asp
    290                 295                 300
```

```
<210> SEQ ID NO 18
<211> LENGTH: 327
<212> TYPE: PRT
<213> ORGANISM: Artificial sequence
<220> FEATURE:
<223> OTHER INFORMATION: GGS variant

<400> SEQUENCE: 18

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
                20                  25                  30

His Asn Ile Arg Glu His Leu Ile Ala Ala Phe Gly Ala Val Ile Lys
            35                  40                  45

Val Asp Lys Ser Asp Leu Glu Thr Ile Ser His Ile Thr Lys Ile Leu
50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Asp Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
    130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Gly Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 19
<211> LENGTH: 327
<212> TYPE: PRT
<213> ORGANISM: Artificial sequence
<220> FEATURE:
<223> OTHER INFORMATION: GGS variant
```

```
<400> SEQUENCE: 19

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
                20                  25                  30

His Asn Ile Arg Glu His Leu Ile Ala Ala Phe Gly Ala Val Ile Lys
            35                  40                  45

Val Asp Lys Ser Asp Leu Glu Thr Ile Ser His Ile Thr Lys Ile Leu
50                  55                  60

His Asn Ser Ser Leu Leu Val Asp Val Glu Asp Asn Ser Met Leu
65                  70                  75                  80

Arg Arg Gly Leu Pro Ala Ala His Cys Leu Phe Asn Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 20
<211> LENGTH: 327
<212> TYPE: PRT
<213> ORGANISM: Artificial sequence
<220> FEATURE:
<223> OTHER INFORMATION: GGS variant

<400> SEQUENCE: 20

Met Asp Tyr Asn Ser Ala Asp Phe Lys Glu Ile Trp Gly Lys Ala Ala
1               5                   10                  15
```

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
50                  55                  60

His Asn Ser Ser Leu Leu Val Asp Val Glu Asp Asn Ser Met Leu
65                  70                  75                  80

Arg Arg Gly Leu Pro Ala Ala His Cys Leu Phe Gln Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
130                 135                 140

Thr Cys Pro Ser Glu Asp Glu Tyr Leu Glu Met Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Gly His Asp Val Ser Lys Leu
290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 21
<211> LENGTH: 327
<212> TYPE: PRT
<213> ORGANISM: Artificial sequence
<220> FEATURE:
<223> OTHER INFORMATION: GGS variant

<400> SEQUENCE: 21

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
 50                  55                  60

His Asn Ser Ser Leu Leu Val Asp Asp Val Glu Asp Asn Ser Met Leu
 65                  70                  75                  80

Arg Arg Gly Leu Pro Ala Ala His Cys Leu Phe Gly Val Pro Gln Thr
                 85                  90                  95

Ile Asn Ser Gly Asn Tyr Met Tyr Phe Val Ala Leu Gln Glu Val Leu
                100                 105                 110

Lys Leu Lys Ser Tyr Asp Ala Val Ser Ile Phe Thr Glu Glu Met Ile
            115                 120                 125

Asn Leu His Arg Gly Gln Gly Met Asp Leu Tyr Trp Arg Glu Thr Leu
130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 22
<211> LENGTH: 327
<212> TYPE: PRT
<213> ORGANISM: Artificial sequence
<220> FEATURE:
<223> OTHER INFORMATION: GGS variant

<400> SEQUENCE: 22

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
    50                  55                  60

His Asn Ser Ser Leu Leu Val Asp Asp Val Glu Asp Asn Ser Met Leu
65                  70                  75                  80

```
Arg Arg Gly Leu Pro Ala Ala His Cys Leu Phe Gly Val Pro Gln Thr
                85                  90                  95

Ile Asn Ser Phe Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
    130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 23
<211> LENGTH: 327
<212> TYPE: PRT
<213> ORGANISM: Artificial sequence
<220> FEATURE:
<223> OTHER INFORMATION: GGS variant

<400> SEQUENCE: 23

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
    50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Tyr Asn Tyr Met Tyr Phe Val Ala Leu Gln Glu Val Leu
            100                 105                 110
```

Lys Leu Lys Ser Tyr Asp Ala Val Ser Ile Phe Thr Glu Glu Met Ile
            115                 120                 125

Asn Leu His Arg Gly Gln Gly Met Asp Leu Tyr Trp Arg Glu Thr Leu
    130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Tyr Leu Asn Leu
    195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
            245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
            275                 280                 285

Ser Tyr Ile Asp Asp Leu Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
            325

<210> SEQ ID NO 24
<211> LENGTH: 327
<212> TYPE: PRT
<213> ORGANISM: Artificial sequence
<220> FEATURE:
<223> OTHER INFORMATION: GGS variant

<400> SEQUENCE: 24

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
    50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Ile Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
            115                 120                 125

Asn Leu His Arg Gly Gln Gly Met Asp Leu Tyr Trp Arg Glu Thr Leu
    130                 135                 140

```
Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
            165                 170                 175

Lys Gln Glu Asp His Glu Lys Ile Asn Phe Asp Leu Thr His Leu Thr
        180                 185                 190

Asp Thr Leu Gly Val Ile Tyr Gln Ile Leu Asp Tyr Leu Asn Leu
        195                 200                 205

Gln Ser Thr Glu Leu Thr Glu Asn Lys Gly Phe Cys Glu Asp Ile Ser
        210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Ala Gly His Asp Val Ser Lys Leu
        290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325
```

```
<210> SEQ ID NO 25
<211> LENGTH: 327
<212> TYPE: PRT
<213> ORGANISM: Artificial sequence
<220> FEATURE:
<223> OTHER INFORMATION: GGS variant

<400> SEQUENCE: 25
```

```
Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
50                  55                  60

His Asn Ser Ser Leu Leu Val Asp Val Glu Asp Asn Ser Met Leu
65                  70                  75                  80

Arg Arg Gly Leu Pro Ala Ala His Cys Leu Phe Gly Val Pro Gln Thr
            85                  90                  95

Ile Asn Ser Leu Asn Tyr Met Tyr Phe Val Ala Leu Gln Glu Val Leu
        100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
            165                 170                 175
```

```
Lys Gln Glu Asp His Glu Lys Ile Asn Phe Asp Leu Thr His Leu Thr
                180                 185                 190

Asp Thr Leu Gly Val Ile Tyr Gln Ile Leu Asp Asp Tyr Leu Asn Leu
            195                 200                 205

Gln Ser Thr Glu Leu Thr Glu Asn Lys Gly Phe Cys Glu Asp Ile Ser
        210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 26
<211> LENGTH: 327
<212> TYPE: PRT
<213> ORGANISM: Artificial sequence
<220> FEATURE:
<223> OTHER INFORMATION: GGS variant

<400> SEQUENCE: 26

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
    50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
    130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205
```

```
Gln Ser Thr Glu Leu Thr Glu Asn Lys Gly Phe Cys Glu Asp Ile Ser
    210                 215                 220
Glu Gly Lys Phe Ser Phe Pro Leu Ile His Ala Ile Arg Thr Asn Pro
225                 230                 235                 240
Asp Asn His Glu Ile Leu Asn Ile Leu Lys Gln Arg Thr Ser Asp Ala
                245                 250                 255
Ser Leu Lys Lys Tyr Ala Val Asp Tyr Met Arg Thr Glu Thr Lys Ser
                260                 265                 270
Phe Asp Tyr Cys Leu Lys Arg Ile Gln Ala Met Ser Leu Lys Ala Ser
            275                 280                 285
Ser Tyr Ile Asp Asp Leu Ala Ala Ala Gly His Asp Val Ser Lys Leu
    290                 295                 300
Arg Ala Ile Leu His Tyr Phe Val Ser Thr Ser Asp Cys Glu Glu Arg
305                 310                 315                 320
Lys Tyr Phe Glu Asp Ala Gln
                325

<210> SEQ ID NO 27
<211> LENGTH: 327
<212> TYPE: PRT
<213> ORGANISM: Artificial sequence
<220> FEATURE:
<223> OTHER INFORMATION: GGS variant

<400> SEQUENCE: 27

Met Asp Tyr Asn Ser Ala Asp Phe Lys Glu Ile Trp Gly Lys Ala Ala
1               5                   10                  15
Asp Thr Ala Leu Leu Gly Pro Tyr Asn Tyr Leu Ala Asn Asn Arg Gly
                20                  25                  30
His Asn Ile Arg Glu His Leu Ile Ala Ala Phe Gly Ala Val Ile Lys
            35                  40                  45
Val Asp Lys Ser Asp Leu Glu Thr Ile Ser His Ile Thr Lys Ile Leu
    50                  55                  60
His Asn Ser Ser Leu Leu Val Asp Asp Val Glu Asp Asn Ser Met Leu
65                  70                  75                  80
Arg Arg Gly Leu Pro Ala Ala His Cys Leu Phe Gly Val Pro Gln Thr
                85                  90                  95
Ile Asn Ser Ala Asn Tyr Met Tyr Phe Val Ala Leu Gln Glu Val Leu
                100                 105                 110
Lys Leu Lys Ser Tyr Asp Ala Val Ser Ile Phe Thr Glu Glu Met Ile
            115                 120                 125
Asn Leu His Arg Gly Gln Gly Met Asp Leu Tyr Trp Arg Glu Thr Leu
    130                 135                 140
Thr Cys Pro Ser Glu Asp Glu Tyr Leu Glu Met Val His Lys Thr
145                 150                 155                 160
Gly Gly Leu Phe Arg Leu Ala Leu Arg Leu Met Leu Ser Val Ala Ser
                165                 170                 175
Lys Gln Glu Asp His Glu Lys Ile Asn Phe Asp Leu Thr His Leu Thr
            180                 185                 190
Asp Thr Leu Gly Val Ile Tyr Gln Ile Leu Asp Asp Tyr Leu Asn Leu
    195                 200                 205
Gln Ser Thr Glu Leu Thr Glu Asn Lys Gly Phe Cys Glu Asp Ile Ser
    210                 215                 220
Glu Gly Lys Phe Ser Phe Pro Leu Ile His Gly Ile Arg Thr Asn Pro
225                 230                 235                 240
```

```
Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
            275                 280                 285

Ser Tyr Ile Asp Asp Leu Ala Ala Gly His Asp Val Ser Lys Leu
            290                 295             300

Arg Ala Ile Leu His Tyr Phe Val Ser Thr Ser Asp Cys Glu Glu Arg
305                 310                 315                 320

Lys Tyr Phe Glu Asp Ala Gln
                325
```

<210> SEQ ID NO 28
<211> LENGTH: 327
<212> TYPE: PRT
<213> ORGANISM: Artificial sequence
<220> FEATURE:
<223> OTHER INFORMATION: GGS variant

<400> SEQUENCE: 28

```
Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
            35                  40                  45

Val Asp Lys Ser Asp Leu Glu Thr Ile Ser His Ile Thr Lys Ile Leu
50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
            115                 120                 125

Asn Leu His Arg Gly Gln Gly Met Asp Leu Tyr Trp Arg Glu Thr Leu
130                 135                 140

Thr Cys Pro Ser Glu Asp Glu Tyr Leu Glu Met Val His Lys Thr
145                 150                 155                 160

Gly Gly Leu Phe Arg Leu Ala Leu Arg Leu Met Leu Ser Val Ala Ser
            165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
            195                 200                 205

Gln Ser Thr Glu Leu Thr Glu Asn Lys Gly Phe Cys Glu Asp Ile Ser
            210                 215                 220

Glu Gly Lys Phe Ser Phe Pro Leu Ile His Gln Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270
```

```
Phe Asp Tyr Cys Leu Lys Arg Ile Gln Ala Met Ser Leu Lys Ala Ser
            275                 280                 285

Ser Tyr Ile Asp Asp Leu Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 29
<211> LENGTH: 327
<212> TYPE: PRT
<213> ORGANISM: Artificial sequence
<220> FEATURE:
<223> OTHER INFORMATION: GGS variant

<400> SEQUENCE: 29

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
130                 135                 140

Thr Cys Pro Ser Glu Asp Glu Tyr Leu Glu Met Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Val Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Gly His Asp Val Ser Lys Leu
    290                 295                 300
```

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 30
<211> LENGTH: 327
<212> TYPE: PRT
<213> ORGANISM: Artificial sequence
<220> FEATURE:
<223> OTHER INFORMATION: GGS variant

<400> SEQUENCE: 30

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
210                 215                 220

Glu Gly Lys Phe Ser Phe Pro Leu Ile His Asp Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Ala Gly His Asp Val Ser Lys Leu
290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

```
<210> SEQ ID NO 31
<211> LENGTH: 327
<212> TYPE: PRT
<213> ORGANISM: Artificial sequence
<220> FEATURE:
<223> OTHER INFORMATION: GGS variant

<400> SEQUENCE: 31

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
    50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
    130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Glu Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325

<210> SEQ ID NO 32
<211> LENGTH: 327
<212> TYPE: PRT
<213> ORGANISM: Artificial sequence
<220> FEATURE:
```

<223> OTHER INFORMATION: GGS variant

<400> SEQUENCE: 32

```
Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
210                 215                 220

Glu Gly Lys Phe Ser Phe Pro Leu Ile His Phe Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Ala Gly His Asp Val Ser Lys Leu
290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325
```

<210> SEQ ID NO 33
<211> LENGTH: 327
<212> TYPE: PRT
<213> ORGANISM: Artificial sequence
<220> FEATURE:
<223> OTHER INFORMATION: GGS variant

<400> SEQUENCE: 33

```
Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45

Val Asp Lys Ser Asp Leu Glu Thr Ile Ser His Ile Thr Lys Ile Leu
50                      55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Tyr Ile Arg Thr Asn Pro
225                 230                 235                 240

Asp Asn His Glu Ile Leu Asn Ile Leu Lys Gln Arg Thr Ser Asp Ala
            245                 250                 255

Ser Leu Lys Lys Tyr Ala Val Asp Tyr Met Arg Thr Glu Thr Lys Ser
        260                 265                 270

Phe Asp Tyr Cys Leu Lys Arg Ile Gln Ala Met Ser Leu Lys Ala Ser
    275                 280                 285

Ser Tyr Ile Asp Asp Leu Ala Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325
```

GERANYLGERANYL PYROPHOSPHATE SYNTHASES

CROSS-REFERENCE TO RELATED APPLICATIONS

This application is a National Stage entry of International Application No. PCT/EP2017/077439, filed 26 Oct. 2017, which claims priority to European Patent Application No. 16196095.0, filed 27 Oct. 2016.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-501000_ST25.txt" created on 8 Apr. 2019, and 83,852 bytes in size) is submitted concurrently with the instant application, and the entire contents of the Sequence Listing are incorporated herein by reference.

FIELD

The present disclosure relates to a variant polypeptide having geranylgeranyl pyrophosphate synthase activity and to a nucleic acid comprising a sequence encoding such a polypeptide. The disclosure also relates to a nucleic acid construct comprising the nucleic acid and to an expression vector comprising the nucleic acid or nucleic acid construct. Further, the disclosure relates to a recombinant host comprising the nucleic acid, a nucleic acid construct or expression vector. The disclosure also relates to a process for the preparation of steviol or a steviol glycoside which comprises fermenting a recombinant host, to a fermentation broth obtainable by such a process and to a steviol glycoside obtained by a process or obtained from the fermentation broth. In addition, the disclosure relates to a composition comprising two or more of the steviol glycosides and to a foodstuff, feed or beverage which comprises the steviol glycoside or composition. Further, the disclosure relates to a method for converting a first steviol glycoside into a second steviol glycoside and to a method for the production of a variant polypeptide having geranylgeranyl pyrophosphate synthase activity

BACKGROUND

The leaves of the perennial herb, *Stevia rebaudiana* Bert. accumulate quantities of intensely sweet compounds known as steviol glycosides. Whilst the biological function of these compounds is unclear, they have commercial significance as alternative high potency sweeteners.

These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in *Stevia* leaves where they may comprise from 10 to 20% of the leaf dry weight. Stevioside and rebaudioside A are both heat and pH stable and suitable for use in carbonated beverages and can be applied in many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in *Stevia* leaves. It may be about 200 times sweeter than sucrose. Rebaudioside M is a further high-potency diterpene glycoside sweetener. It is present in trace amounts in certain *stevia* variety leaves, but has been suggested to have a superior taste profile.

Steviol glycosides have traditionally been extracted from the *Stevia* plant. In the *Stevia* plant, (−)-kaurenoic acid, an intermediate in gibberellic acid (GA) biosynthesis, is converted into the tetracyclic diterpene steviol, which then proceeds through a multi-step glycosylation pathway to form the various steviol glycosides. However, yields may be variable and affected by agriculture and environmental conditions. Also, *Stevia* cultivation requires substantial land area, a long time prior to harvest, intensive labour and additional costs for the extraction and purification of the glycosides.

More recently, interest has grown in producing steviol glycosides using fermentative processes. WO2013/110673 and WO2015/007748 describe microorganisms that may be used to produce at least the steviol glycosides rebaudioside A and rebaudioside D.

Further improvement of such microorganisms is desirable in order that higher amounts of steviol glycosides may be produced and/or additional or new steviol glycosides and/or higher amounts of specific steviol glycosides and/or mixtures of steviol glycosides having desired ratios of different steviol glycosides may be produced.

SUMMARY

The present disclosure is based on the identification of variant geranylgeranyl pyrophosphate synthases. These variants may be used in the production of recombinant hosts suitable for the production of steviol and/or one or more steviol glycosides.

Such recombinant hosts may produce higher amounts of steviol glycosides as compared with recombinant hosts expressing a non-variant geranylgeranyl pyrophosphate synthase. Production of higher amounts of steviol glycosides may make recovery of steviol glycosides easier. Alternatively or in addition, a higher yield may be obtained.

Accordingly, the disclosure relates to a variant polypeptide having geranylgeranyl pyrophosphate synthase activity, which variant polypeptide comprises an amino acid sequence which, when aligned with a geranylgeranyl pyrophosphate synthase comprising the sequence set out in SEQ ID NO: 1 (the wild type GGS sequence from *Yarrowia lipolytica*), comprises at least one substitution of an amino acid residue corresponding to any of amino acids at positions:

92, 100 or 235 said positions being defined with reference to SEQ ID NO: 1 and wherein the variant has one or more modified properties as compared with a reference polypeptide having geranylgeranyl pyrophosphate synthase activity.

The disclosure also relates to:

a variant polypeptide having geranylgeranyl pyrophosphate synthase activity comprising an amino acid sequence having at least about 95% sequence identity, at least about 96%, at least about 97%, at least about 98% or at least about 99% sequence identity to any one of SEQ ID NOs: 3, 5, 7, 9, 11, 13 or 15;

a nucleic acid comprising a sequence encoding a variant polypeptide as disclosed herein;

a nucleic acid construct comprising the nucleic acid as disclosed herein, operably linked to one or more control sequences capable of directing the expression of a geranylgeranyl pyrophosphate synthase in a suitable expression host;

an expression vector comprising a nucleic acid or a nucleic acid construct as disclosed herein;

a recombinant host comprising a nucleic acid, a nucleic acid construct or an expression vector as disclosed herein;

a process for the preparation of steviol or a steviol glycoside which comprises fermenting a recombinant host as disclosed herein in a suitable fermentation medium and, optionally, recovering the steviol or steviol glycoside;

a fermentation broth comprising a steviol glycoside obtainable by the process for the preparation of steviol or steviol glycoside as disclosed herein;

a steviol glycoside obtained by a process for the preparation of steviol or steviol glycoside as disclosed herein or obtained from a fermentation broth comprising a steviol glycoside as disclosed herein;

a composition comprising two or more steviol glycosides obtained by a process for the preparation of steviol or steviol glycoside as disclosed herein or obtained from a fermentation broth comprising a steviol glycoside as disclosed herein;

a foodstuff, feed or beverage which comprises a steviol glycoside obtained by a process for the preparation of steviol or steviol glycoside as disclosed herein or obtained from a fermentation broth comprising a steviol glycoside as disclosed herein or a food stuff, feed or beverage which comprises a composition as disclosed herein;

a method for converting a first steviol glycoside into a second steviol glycoside, which method comprises:
  contacting said first steviol glycoside with a recombinant host as disclosed herein, a cell free extract derived from such a recombinant host or an enzyme preparation derived from either thereof;
  thereby to convert the first steviol glycoside into the second steviol glycoside; and a method for producing a geranylgeranyl pyrophosphate synthase comprising cultivating a host cell as disclosed herein under conditions suitable for production of the geranylgeranyl pyrophosphate synthase and, optionally, recovering the geranylgeranyl pyrophosphate synthase.

BRIEF DESCRIPTION OF THE DRAWINGS

FIG. 1 sets out a schematic diagram of the potential pathways leading to biosynthesis of steviol glycosides.

DESCRIPTION OF THE SEQUENCE LISTING

A description of the sequences is set out in Table 1.

TABLE 1

| Description | SEQ ID NO |
| --- | --- |
| *Yarrowia lipolytica* GGPS | SEQ ID NO: 1 |
| CDS *Yarrowia lipolytica* GGPS | SEQ ID NO: 2 |
| *Yarrowia lipolytica* GGPS with Gly92Glu mutation | SEQ ID NO: 3 |
| CDS *Yarrowia lipolytica* GGPS with Gly92Glu mutation | SEQ ID NO: 4 |
| *Yarrowia lipolytica* GGPS with Ala100Val mutation | SEQ ID NO: 5 |

TABLE 1-continued

| Description | SEQ ID NO |
| --- | --- |
| CDS *Yarrowia lipolytica* GGPS with Ala100Val mutation | SEQ ID NO: 6 |
| *Yarrowia lipolytica* GGPS with Ser235Asn mutation | SEQ ID NO: 7 |
| CDS *Yarrowia lipolytica* GGPS with Ser235Asn mutation | SEQ ID NO: 8 |
| *Yarrowia lipolytica* GGPS with Gly92Glu + Ala100Val mutation | SEQ ID NO: 9 |
| CDS *Yarrowia lipolytica* GGPS with Gly92Glu + Ala100Val mutation | SEQ ID NO: 10 |
| *Yarrowia lipolytica* GGPS with Gly92Glu + Ser235Asn mutation | SEQ ID NO: 11 |
| CDS *Yarrowia lipolytica* GGPS with Gly92Glu + Ser235Asn mutation | SEQ ID NO: 12 |
| *Yarrowia lipolytica* GGPS with Ala100Val + Ser235Asn mutation | SEQ ID NO: 13 |
| CDS *Yarrowia lipolytica* GGPS with Ala100Val + Ser235Asn mutation | SEQ ID NO: 14 |
| *Yarrowia lipolytica* GGPS with Gly92Glu + Ala100Val + Ser235Asn mutation | SEQ ID NO: 15 |
| CDS *Yarrowia lipolytica* GGPS with Gly92Glu + Ala100Val + Ser235Asn mutation | SEQ ID NO: 16 |
| *Mucor circinelloides* GGPS | SEQ ID NO: 17 |
| *Yarrowia lipolytica* GGPS with Gly92Asp mutation | SEQ ID NO: 18 |
| *Yarrowia lipolytica* GGPS with Gly92Asn mutation | SEQ ID NO: 19 |
| *Yarrowia lipolytica* GGPS with Gly92Gln mutation | SEQ ID NO: 20 |
| *Yarrowia lipolytica* GGPS with Ala100Gly mutation | SEQ ID NO: 21 |
| *Yarrowia lipolytica* GGPS with Ala100Phe mutation | SEQ ID NO: 22 |
| *Yarrowia lipolytica* GGPS with Ala100Tyr mutation | SEQ ID NO: 23 |
| *Yarrowia lipolytica* GGPS with Ala100Ile mutation | SEQ ID NO: 24 |
| *Yarrowia lipolytica* GGPS with Ala100Leu mutation | SEQ ID NO: 25 |
| *Yarrowia lipolytica* GGPS with Ser235Ala mutation | SEQ ID NO: 26 |
| *Yarrowia lipolytica* GGPS with Ser235Gly mutation | SEQ ID NO: 27 |
| *Yarrowia lipolytica* GGPS with Ser235Gln mutation | SEQ ID NO: 28 |
| *Yarrowia lipolytica* GGPS with Ser235Val mutation | SEQ ID NO: 29 |
| *Yarrowia lipolytica* GGPS with Ser235Asp mutation | SEQ ID NO: 30 |
| *Yarrowia lipolytica* GGPS with Ser235Glu mutation | SEQ ID NO: 31 |
| *Yarrowia lipolytica* GGPS with Ser235Phe mutation | SEQ ID NO: 32 |
| *Yarrowia lipolytica* GGPS with Ser235Tyr mutation | SEQ ID NO: 33 |

DETAILED DESCRIPTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

Herein, "rebaudioside" may be shortened to "reb". That is to say, rebaudioside A and reb A, for example, are intended to indicate the same molecule.

The disclosure concerns new polypeptides having geranylgeranyl pyrophosphate synthase activity. Recombinant hosts expressing such a polypeptide, i.e. a host cell comprising a recombinant sequence encoding such a polypeptide, may be used for the production of steviol glycosides. The ability of a given recombinant host to produce a steviol glycoside may be a property of the host in non-recombinant form or may be a result of the introduction of one or more recombinant nucleic acid sequences (i.e. encoding enzymes leading to the production of a steviol glycoside). A recombinant host as disclosed herein may be capable of increased production of a steviol glycoside in comparison to a non-recombinant host or a recombinant host capable of expressing a reference polypeptide having geranylgeranyl pyrophosphate synthase activity.

According to the present disclosure, there is thus provided a variant polypeptide having geranylgeranyl pyrophosphate synthase activity.

A variant polypeptide according to the disclosure has geranylgeranyl pyrophosphate synthase activity. Geranylgeranyl pyrophosphate synthase (or geranylgeranyl diphosphate synthase activity) is a term well known to the skilled person.

For the purpose of this disclosure, a polypeptide having geranylgeranyl pyrophosphate synthase (or synthetase) activity is typically one which catalyzes the synthesis of GGPP from farnesyl diphosphate and isopentenyl diphosphate.

Geranylgeranyl pyrophosphate synthase activity may also be referred to as GGPP synthase activity, GGPP synthetase activity, GGPPS activity, GGPS activity, GGS activity, GGS1 activity, GGPS1 activity or GGPPS1 activity.

Geranylgeranyl pyrophosphate synthase activity may also be defined in terms of activity of the product of the carG gene of *Mucor circinelloides*. The product of the carG gene of *Mucor circinelloides* may catalyze one or more of:
dimethylallyl diphosphate+isopentenyl diphosphate=diphosphate+geranyl diphosphate; geranyl diphosphate+isopentenyl diphosphate=diphosphate+(2E,6E)-farnesyl diphosphate; or -(2E,6E)-farnesyl diphosphate+isopentenyl diphosphate=diphosphate+geranylgeranyl diphosphate.

Any of these catalytic activities may be used to define a geranylgeranyl pyrophosphate synthase of the disclosure.

Thus, for the purposes of the present disclosure, a polypeptide having geranylgeranyl pyrophosphate synthase activity may be one which is capable of catalysing or partially catalyzing the formation of geranylgeranyl pyrophosphate.

A variant polypeptide as disclosed herein has modified geranylgeranyl pyrophosphate synthase activity as compared with a reference polypeptide having geranylgeranyl pyrophosphate synthase activity.

Such a variant polypeptide may have a decreased specific geranylgeranyl pyrophosphate synthase activity as compared with the reference polypeptide.

Such a variant polypeptide may have an increased specific geranylgeranyl pyrophosphate synthase activity as compared with the reference polypeptide.

A variant polypeptide according to the disclosure may be a non-naturally occurring polypeptide.

Herein, variant polypeptides of the disclosure may be referred to as a "geranylgeranyl pyrophosphate synthase variant", "GGPS" or "GGS", "GGPS variant", "GGS variant", "variant polypeptide" or "GGPS polypeptide" or "GGS polypeptide" or the like.

A GGPS variant polypeptide having geranylgeranyl pyrophosphate synthase activity as disclosed herein may be a variant of a reference polypeptide having geranylgeranyl pyrophosphate synthase activity which variant polypeptide comprises an amino acid sequence which, when aligned with a geranylgeranyl pyrophosphate synthase comprising the sequence set out in SEQ ID NO: 1, comprises at least one substitution of an amino acid residue corresponding to any of amino acids at positions
92, 100 or 235,
said positions being defined with reference to SEQ ID NO: 1.

A GGPS variant polypeptide as disclosed herein (for example a variant having one or more substitution as set out herein) may have at least about 60%, 70%, 80% identity with the reference GGPS polypeptide, such as the GGPS of SEQ ID NO: 1, for example at least about 85% identity with the reference polypeptide, such as at least about 90% identity with the reference polypeptide, at least about 95% identity with the reference polypeptide, at least about 98% identity with the reference polypeptide or at least about 99% identity with the reference polypeptide. Such a variant will typically have one or more substitution or sets of substitutions selected from a position corresponding to
92, 100 or 235
as defined with reference to SEQ ID NO: 1.

A GGPS variant polypeptide as disclosed herein may be a variant of the polypeptide set out in SEQ ID NO: 1, having a substitution at one or more of positions 92, 100 or 235.

An amino acid position corresponding to one of the positions defined herein in the reference GGPS may be a position that aligns in a multiple (protein) sequence alignment with any of the stated amino acid positions.

Accordingly, a GGPS variant polypeptide as disclosed herein may be a variant of the polypeptide set out in SEQ ID NO: 17 having a substitution at one or more of positions 89, 97 or 225.

The inventors have surprisingly found that recombinant host cells expressing a variant polypeptide as disclosed herein and having a substitution at one or more of positions 92, 100 or 235, when used in methods for producing steviol glycosides, produced significantly higher titers of steviol glycosides and KA-glycosides compared to recombinant host cells expressing the reference polypeptide.

Two of the three positions where the substitutions according to the present disclosure may occur i.e. 92 and 100, respectively, as defined with reference to SEQ ID NO: 1, are expected to be located in a hinge point on top of an alpha helix (position 92) and in an alpha-helix (position 100), respectively, that are expected to be located in the protein homo dimer interphase. A phylogenetic analysis indicated that positions homologous to glycine 92 are highly conserved. Without being bound by a theory, the inventors believe that the surprising results observed might be due to the fact that the mutation of the strictly conserved glycine 92 to e.g. glutamic acid is likely to have an effect on protein structure and potentially dimer interaction. In phylogeny, little amino acid variation has been observed at positions homologous to A100 but amino acid variation to larger hydrophobic residues like valine has not been observed. Without being bound by a theory, the inventors believe that the surprising results observed in the examples might be due to the fact that the Ala100Val mutation might have an effect on the dimer interphase and affect the active site and catalysis by steric interaction with a neighboring alpha-helix that is part of the substrate binding pocket.

The third position where a mutation may occur, i.e. 235, might be located in an alpha-helix that is remote from the two positions described earlier and not involved in protein-protein interactions. Phylogenetic analysis indicated that serine occurs at position homologous to Ser235 but that alanine is the most predominant amino acid at this position.

A GGPS variant of the disclosure will typically retain GGPS activity. That is to say, a GGPS variant according to the disclosure will typically be capable of catalysing the reaction set out above, albeit with a modified activity as compared with a reference polypeptide.

A suitable reference polypeptide may be a polypeptide comprising the amino acid sequence of SEQ ID NO: 1 (*Yarrowia lipolytica*), SEQ ID NO: 17 (*Mucor circinelloides*) or the amino acid sequence of a GGPS from *S. cerevisiae*.

Preferably, a GGPS variant polypeptide according to the disclosure will typically exhibit improved properties in comparison with the reference polypeptide from which it is derived, typically in terms of specific activity and/or substrate specificity. Such an improved property will typically be one which is relevant if the variant were to be used as set out below, for example in a method for the production of steviol and/or a steviol glycoside (by expressing the GGPS in a recombinant host).

Thus, a GGPS variant according to the disclosure is one which is typically capable of increasing production of steviol and/or a steviol glycoside in a recombinant host capable of the production of said steviol and/or a steviol glycoside (in comparison with a recombinant host capable of the production of steviol and/or a steviol glycoside which expresses the reference polypeptide). That is to say, overexpression of a GGPS variant polypeptide according to the disclosure in a host cell will typically lead to increased production of steviol and/or a steviol glycoside as compared to a host cell which overexpresses a reference polypeptide (such as the GGPS of SEQ ID NO: 1 or SEQ ID NO: 17).

A GGPS variant which exhibits a property which is improved in relation to the reference GGPS is one which demonstrates a measurable reduction or increase in the relevant property, for example specific activity, typically such that the GGPS variant is more suited to a use as set out herein, for example in a method for the production of steviol or a steviol glycoside.

A GGPS variant polypeptide comprises an amino acid sequence that has one or more substitution, deletion and/or insertion of an amino acid as compared to the reference polypeptide and/or one or more truncations as compared to the reference polypeptide. A GGPS variant polypeptide may comprise one or more of the substitutions described herein.

A variant polypeptide having GGPS activity, for example as set out herein, which variant polypeptide has an amino acid sequence which, when aligned with the GGPS comprising the sequence set out in SEQ ID NO: 1, comprises at least one substitution of an amino acid residue corresponding to any of amino acids 92, 100 or 235 said positions being defined with reference to SEQ ID NO: 1 and wherein the variant has one or more modified properties as compared with a reference polypeptide having GGPS activity.

Thus, the amino acid present at one or more of the said positions will be replaced with a different amino acid than appears at that position in the reference sequence (the positions being defined with reference to SEQ ID NO: 1).

A variant GGPS according to the disclosure may comprise one of the substitutions set out above. However, a variant polypeptide may comprise any combination of substitutions at positions 92, 100 or 235, said positions being defined with reference to a suitable reference sequence such as that set out in SEQ ID NO: 1, such as two of the substitutions or all of the substitutions at the said positions.

A variant GGPS may comprise a substitution at position 92 as defined with reference to SEQ ID NO: 1. The substitution may be such that an amino acid residue selected from a Glu residue, an Asp residue, an Asn residue, a Gln residue, preferably a Glu residue, is at this position.

Therefore, in one embodiment the variant polypeptide having GGPS activity as disclosed herein comprises an amino acid sequence which, when aligned with a geranylgeranyl pyrophosphate synthase comprising the sequence set out in SEQ ID NO: 1, comprises a substitution of the amino acid residue corresponding to amino acid at position 92 with an amino acid residue selected from a Glu residue, an Asp residue, an Asn residue, a Gln residue, preferably with a Glu residue, said positions being defined with reference to SEQ ID NO: 1 and wherein the variant has one or more modified properties as compared with a reference polypeptide having geranylgeranyl pyrophosphate synthase activity.

A variant GGPS may comprise a substitution at position 100 as defined with reference to SEQ ID NO: 1. The substitution may be such that a Val residue, a Gly residue, a Phe residue, a Tyr residue, a Ile residue, a Leu residue, preferably a Val residue is at this position.

Therefore, in one embodiment the variant polypeptide having GGPS activity as disclosed herein comprises an amino acid sequence which, when aligned with a geranylgeranyl pyrophosphate synthase comprising the sequence set out in SEQ ID NO: 1, comprises a substitution of the amino acid residue corresponding to amino acid at position 100 with an amino acid residue selected from a Val residue, a Gly residue, a Phe residue, a Tyr residue, a Ile residue, a Leu residue, preferably a Val residue, said positions being defined with reference to SEQ ID NO: 1 and wherein the variant has one or more modified properties as compared with a reference polypeptide having geranylgeranyl pyrophosphate synthase activity.

A variant GGPS may comprise a substitution at position 235 as defined with reference to SEQ ID NO: 1. The substitution may be such that a Asn residue, a Ala residue, a Gly residue, a Gln residue, a Val residue, a Asp residue, a Glu residue, a Phe residue, a Tyr residue, preferably a Asn residue, is at this position.

Therefore, in one embodiment the variant polypeptide having GGPS activity as disclosed herein comprises an amino acid sequence which, when aligned with a geranylgeranyl pyrophosphate synthase comprising the sequence set out in SEQ ID NO: 1, comprises a substitution of the amino acid residue corresponding to amino acid at position 235 with an amino acid residue selected from a Asn residue, a Ala residue, a Gly residue, a Gln residue, a Val residue, a Asp residue, a Glu residue, a Phe residue, a Tyr residue, preferably a Asn residue, said positions being defined with reference to SEQ ID NO: 1 and wherein the variant has one or more modified properties as compared with a reference polypeptide having geranylgeranyl pyrophosphate synthase activity.

A variant GGPS may comprise a substitution at positions 92 and 100 as defined with reference to SEQ ID NO: 1. The substitutions may be such that a Glu and a Val residue are at these positions respectively. In other embodiments, the substitutions may be such that a Glu and a Gly, or a Glu and a Phe, or a Glu and a Tyr, or a Glu and a Ile, or a Glu and a Leu are at these positions respectively. In other embodiments, the substitution at position 92 and 100 as defined with reference to SEQ ID NO: 1 may be such that a Asp and a Val are at these position respectively, or a Asp and a Gly, or a Asp and a Phe, or a Asp and a Tyr, or a Asp and a Ile, or a Asp and a Leu, or a Asn and a Val, or a Asn and a Gly, or a Asn and a Phe, or a Asn and a Tyr, or a Asn and a Ile, or a Asn and a Leu, or a Gln and a Val, or a Gln and a Gly, or a Gln and a Phe, or a Gln and a Tyr, or a Gln and a Ile, or a Gln and a Leu are at these positions.

A variant GGPS may comprise a substitution at positions 92 and 235 as defined with reference to SEQ ID NO: 1. The substitutions may be such that a Glu and a Asn residue are at these positions respectively. In other embodiments, the substitutions may be such that a Glu and a Ala, or a Glu and a Gly, or a Glu and a Gln, or a Glu and a Val, or a Glu and a Asp, or a Glu and a Glu, or a Glu and a Phe, or a Glu and a Tyr are at these positions respectively. In other embodiments, the substitution at position 92 and 235 as defined with reference to SEQ ID NO: 1 may be such that a Asp and a Asn, or a Asp and a Ala, or a Asp and a Gly, or a Asp and a Gln, or a Asp and a Val, or a Asp and a Asp, or a Asp and a Glu or a Asp and a Phe, or a Asp and a Tyr, or a Asn and a Asn, or a Asn and a Ala, or a Asn and a Gly, or a Asn and a Gln, or a Asn and a Val, or a Asn and a Asp, or a Asn and a Glu, or a Asn and a Phe, or a Asn and a Tyr, or a Gln and a Asn, or a Gln and a Ala, or a Gln and a Gly, or a Gln and a Gln, or a Gln and a Val, or a Gln and a Asp, or a Gln and a Glu, or a Gln and a Phe, or a Gln and a Tyr are at these positions.

A variant GGPS may comprise a substitution at positions 100 and 235 as defined with reference to SEQ ID NO: 1. The substitutions may be such that a Val and a Asn residue are at these positions respectively. In other embodiments, the substitutions may be such that a Val and a Ala, or a Val and a Gly, or a Val and a Gln, or a Val and a Val, or a Val and a Asp, or a Val and a Glu, or a Val and a Phe, or a Val and a Tyr are at these positions respectively. In other embodiments, the substitutions may be such that a Gly and a Asn, or a Gly and a Ala, or a Gly and a Gly, or a Gly and a Gln, or a Gly and a Val, or a Gly and a Asp, or a Gly and a Glu, or a Gly and a Phe, or a Gly and a Tyr are at these positions respectively. In other embodiments, the substitution at position 100 and 235 as defined with reference to SEQ ID NO: 1 may be such that a Phe and a Asn, or a Phe and a Ala, or a Phe and a Gly, or a Phe and a Gln, or a Phe and a Val, or a Phe and a Asp, or a Phe and a Glu, or a Phe and a Phe, or a Phe and a Tyr, or a Tyr and a Asn, or a Tyr and a Ala, or a Tyr and a Gly, or a Tyr and a Gln, or a Tyr and a Val, or a Tyr and a Asp, or a Tyr and a Glu, or a Tyr and a Phe, or a Tyr and a Tyr, or a Ile and a Asn, or a Ile and a Ala, or a Ile and a Gly, or a Ile and a Gln, or a Ile and a Val, or a Ile and a Asp, or a Ile and a Glu, or a Ile and a Phe, or a Ile and a Tyr, or a Leu and a Asn, or a Leu and a Ala, or a Leu and a Gly, or a Leu and a Gln, or a Leu and a Val, or a Leu and a Asp, or a Leu and a Glu, or a Leu and a Phe, or a Leu and a Tyr are at these positions.

A variant GGPS may comprise a substitution at positions 92, 100 and 235 as defined with reference to SEQ ID NO: 1. The substitutions may be such that a Glu, a Val and a Asn residue are at these positions respectively. According to embodiments of the disclosure, the combinations of substitutions which may be found in the polypeptide variants according to the present disclosure at position 92, 100 and 235 as defined with reference to SEQ ID NO: 1, respectively are as those indicated hereafter:

each one of 92E+100V or 92E+100G or 92E+100F or 92E+100Y or 92E+100I or 92E+100L or 92D+100V or 92D+100G or 92D+100F or 92D+100Y or 92D+100I or 92D+100L or 92N+100V or 92N+100G or 92N+100F or 92N+100Y or 92N+100I or 92N+100L or 92Q+100V or 92Q+100G or 92Q+100F or 92Q+100Y or 92Q+100I or 92Q+100L, respectively, combined with each one of N, A; G, Q; V; D, E; F; or Y at position 235, respectively; or each one of 92E+235N or 92E+235A or 92E+235G or 92E+235Q or 92E+235V or 92E+235D or 92E+235E or 92E+235F or 92E+235Y or 92D+235N or 92D+235A or 92D+235G or 92D+235Q or 92D+235V or 92D+235D or 92D+235E or 92D+235F or 92D+235Y or 92N+235N or 92N+235A or 92N+235G or 92N+235Q or 92N+235V or 92N+235D or 92N+235E or 92N+235F or 92N+235Y or 92Q+235N or 92Q+235A or 92Q+235G or 92Q+235Q or 92Q+235V or 92Q+235D or 92Q+235E or 92Q+235F or 92Q+235Y, respectively, combined with each one of V, G, F, Y, I, L at position 100, respectively; or each one of 100V+235N or 100V+235A or 100V+235G or 100V+235Q or 100V+235V or 100V+235D or 100V+235E or 100V+235F or 100V+235Y or 100G+235N or 100G+235A or 100G+235G or 100G+235Q or 100G+235V or 100G+235D or 100G+235E or 100G+235F or 100G+235Y or 100F+235N or 100F+235A or 100F+235G or 100F+235Q or 100F+235V or 100F+235D or 100F+235E or 100F+235F or 100F+235Y or 100Y+235N or 100Y+235A or 100Y+235G or 100Y+235Q or 100Y+235V or 100Y+235D or 100Y+235E or 100Y+235F or 100Y+235Y or 100I+235N or 100I+235A or 100I+235G or 100I+235Q or 100I+235V or 100I+235D or 100I+235E or 100I+235F or 100I+235Y or 100L+235N or 100L+235A or 100L+235G or 100L+235Q or 100L+235V or 100L+235D or 100L+235E or 100L+235F or 100L+235Y, respectively, combined with each one of E, D, N, or Q at position 92, respectively.

A GGPS variant polypeptide of the disclosure may be a variant of the polypeptide set out in SEQ ID NO: 17 having a substitution at one or more of positions 89, 97 or 225 of that sequence. Thus, a variant of the disclosure may comprise: substitutions at positions 89 and 97; substitutions at positions 89 and 225; substitutions at positions 97 and 225; or substitutions at positions 89, 97, 225. Preferred substitutions are one or more of Glu, Asp, Asn, or Gln, preferably Glu at position 89, Val, Gly, Phe, Tyr, Ile, or Leu, preferably Val at position 97 and Asn, Ala, Gly, Gln, Val, Asp, Glu, Phe, or Tyr, preferably Asn at position 225.

A variant polypeptide of the disclosure may comprise additional substitutions other than the three positions defined above, for example, one or more additional substitutions, additions or deletions.

A variant of the disclosure may comprise a combination of different types of modification of this sort. A variant may comprise one, two, three, four, at least 5, at least 10, at least 15, at least 20, at least 25, at least 30 or more such modifications (which may all be of the same type or may be different types of modification). Typically, the additional modifications may be substitutions.

Such additional modifications may occur in the hinge region and/or the alpha-helix region referred to above.

A variant polypeptide of the disclosure may comprise the amino acid sequence set out in SEQ ID NOs: 3, 5, 7, 9, 11, 13, 15, or 18 to 33.

A host cell of the disclosure may comprise nucleic acids encoding one, two, three, four, five or more variants of the disclosure. Such variants may be the same or different. A host cell may comprise a nucleic acid encoding the GGPS of SEQ ID NO: 1 and a nucleic acid encoding one or more variants of the disclosure. That is to say, a host cell may comprise a nucleic acid encoding the GGPS of SEQ ID NO: 1 and a nucleic acid encoding one or more variants of the disclosure, each of which may be present in a copy of one, two, three, four, five or more.

A variant polypeptide will typically have modified GGPS activity in comparison to a reference polypeptide. Typically, the modified activity may be defined in terms of steviol and/or steviol glycoside production in a recombinant host.

The modified activity may be defined in terms of an increase in the production of steviol and/or a steviol glycoside when a variant GGPS is overexpressed in a host cell as compared to the production level of an equivalent host cell which overexpresses a reference polypeptide, for example that of SEQ ID NO: 1 or SEQ ID NO: 17.

The modified activity may be defined in terms of a change in ratio of the production of two steviol glycosides, for example the ratio of rebaudioside A:rebaudioside M may be increased or, alternatively, the ratio of rebaudioside M:rebaudioside A may be increased, when a variant GGPS is overexpressed in a host cell as compared to the production level of an equivalent host cell which overexpresses a reference polypeptide, for example that of SEQ ID NO: 1 or SEQ ID NO: 17.

A variant GGPS may be capable of increasing production levels, for example by at least 5%, at least 10%, at least 25%, at least 50%, at least 100% or more. Production levels may be expressed in terms of g/L or mol/L (M), so an increase in the production level of steviol and/or steviol glycosides will be evident by higher level of production in terms of g/L or mol/L.

The word "polypeptide" is used herein for chains containing more than about seven amino acid residues. All polypeptide sequences herein are written from left to right and in the direction from amino terminus to carboxy terminus. The one-letter code of amino acids used herein is commonly known in the art and can be found in Sambrook, et al. (Molecular Cloning: A Laboratory Manual, 2nd ed. Cold Spring Harbor Laboratory, Cold Spring Harbor Laboratory Press, Cold Spring Harbor, N.Y., 1989).

A GGPS variant polypeptide as disclosed herein may be in isolated form, such as substantially isolated form. By "isolated" polypeptide or protein is intended a polypeptide or protein removed from its native environment. For example, recombinantly produced polypeptides and proteins expressed in host cells are considered isolated for the purpose of the disclosure as are recombinant polypeptides which have been substantially purified by any suitable technique. A GGPS variant polypeptide according to the disclosure can be recovered and purified from recombinant cell cultures by methods known in the art.

GGPS variant polypeptides of the present disclosure include products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present disclosure may be glycosylated or may be non-glycosylated. In addition, polypeptides of the disclosure may also include an initial modified methionine residue, in some cases as a result of host-mediated processes.

The present disclosure also features biologically active fragments of the GGPS polypeptide variants according to the disclosure. Such fragments are considered to be encompassed within the term "a GGPS variant according to the disclosure".

Biologically active fragments of a GGPS polypeptide variant include polypeptides comprising amino acid sequences sufficiently identical to or derived from the amino acid sequence of a variant protein as disclosed herein which include fewer amino acids than the full-length protein but which exhibit at least one biological activity of the corresponding full-length protein. Typically, biologically active fragments comprise a domain or motif with at least one activity of a variant protein as disclosed herein. A biologically active fragment of a GGPS variant according to the disclosure can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide according to the disclosure.

Typically, a protein fragment of a GGPS variant as disclosed herein will comprise one or more of the substitutions defined herein.

The disclosure also features nucleic acid fragments which encode the above biologically active fragments (which biologically active fragments are themselves variants of the disclosure).

The present disclosure provides polynucleotides which comprise a sequence encoding a GGPS variant polypeptide as disclosed herein (and biologically active fragments thereof). The disclosure also relates to an isolated polynucleotide encoding at least one functional domain of a GGPS polypeptide variant as disclosed herein. Typically, such a domain will comprise one or more of the substitutions described herein.

A nucleic acid molecule as disclosed herein can be generated using standard molecular biology techniques well known to those skilled in the art taken in combination with the sequence information provided herein. For example, using standard synthetic techniques, the required nucleic acid molecule may be generated by PCR or synthesized de novo. Such a synthetic process will typically be an automated process.

A nucleic acid as disclosed herein may comprise one or more deletions, i.e. gaps, in comparison to a nucleic acid encoding a reference GGPS. Such deletions/gaps may also be generated using site-directed mutagenesis using appropriate oligonucleotides. Techniques for generating such deletions are well known to those skilled in the art.

Furthermore, oligonucleotides corresponding to or hybridizable to nucleotide sequences according to the disclosure can be prepared by standard synthetic techniques, e.g., using an automated DNA synthesizer.

Also, complementary nucleic acids and antisense nucleic acids are included in the present disclosure. A nucleic acid molecule which is complementary to another nucleotide sequence is one which is sufficiently complementary to the other nucleotide sequence such that it can hybridize to the other nucleotide sequence thereby forming a stable duplex.

One aspect of the disclosure pertains to isolated nucleic acid molecules that encode a variant polypeptide of the invention, or a biologically active fragment or domain thereof, as well as nucleic acid molecules sufficient for use as hybridization probes to identify nucleic acid molecules encoding a polypeptide as disclosed herein and fragments of such nucleic acid molecules suitable for use as PCR primers for the amplification or mutation of nucleic acid molecules, such as for the preparation of nucleic acid molecules of the disclosure.

An "isolated nucleic acid" or "isolated polynucleotide" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "nucleic acid", "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The disclosure also relates to a nucleic acid construct comprising a polynucleotide sequence encoding a variant polypeptide according to the disclosure and, linked operably thereto, control sequences permitting expression of the polynucleotide sequence in a host cell. The nucleic acid construct may be incorporated into a vector, such as an expression vector and/or into a host cell in order to effect expression of the variant polypeptide.

The term "nucleic acid construct" is herein referred to as a nucleic acid molecule, either single- or double-stranded, which is isolated from a naturally-occurring gene or, more typically, which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

A promoter that could be used to achieve the expression of a nucleotide sequence coding for an enzyme such as a variant GGPS polypeptide or any other enzyme introduced in recombinant host cell as disclosed herein, may be not native to a nucleotide sequence coding for the enzyme to be expressed, i.e. a promoter that is heterologous to the nucleotide sequence (coding sequence) to which it is operably linked. Preferably, the promoter is homologous, i.e. endogenous to the host cell.

Suitable promoters in this context include both constitutive and inducible natural promoters as well as engineered promoters, which are well known to the person skilled in the art. Suitable promoters in host cells may be GALT, GAL10, or GAL 1, CYC1, HIS3, ADH1, PGL, PH05, GAPDH, ADC1, TRP1, URA3, LEU2, ENO, TPI, and AOX1. Other suitable promoters include PDC, GPD1, PGK1, TEF1, and TDH.

Usually a nucleotide sequence encoding an enzyme comprises a terminator. Any terminator, which is functional in a host cell, may be used in the present disclosure. Preferred terminators are obtained from natural genes of the host cell. Suitable terminator sequences are well known in the art. Preferably, such terminators are combined with mutations that prevent nonsense mediated mRNA decay in the host cell as disclosed herein (see for example: Shirley et al., 2002, Genetics 161:1465-1482).

The disclosure further relates to a vector, preferably an expression vector, comprising a polynucleotide according to the disclosure or a nucleic acid construct according to the disclosure (i.e. comprising sequence encoding a variant GGPS polypeptide as disclosed herein).

In order to facilitate expression and/or translation of the GGPS, the nucleic acid sequence encoding the GGPS may be comprised in an expression vector such that the gene encoding the GGPS is operably linked to the appropriate control sequences for expression and/or translation in vitro, or in a host cell as disclosed herein. The expression vector may be any vector (e.g., a plasmid or virus), which can be conveniently subjected to recombinant DNA procedures and can bring about the expression of the polynucleotide encoding the GGPS variant polypeptide. The choice of the vector will typically depend on the compatibility of the vector with the cell into which the vector is to be introduced. The vectors may be linear or closed circular plasmids. The vector may be an autonomously replicating vector, i. e., a vector, which exists as an extra-chromosomal entity, the replication of which is independent of chromosomal replication, e.g., a plasmid, an extra-chromosomal element, a mini-chromosome, or an artificial chromosome. If intended for use in a host cell of fungal origin, a suitable episomal nucleic acid construct may e.g. be based on the yeast 2μ or pKD1 plasmids (Gleer et al., 1991, Biotechnology 9: 968-975), or the AMA plasmids (Fierro et al., 1995, Curr Genet. 29:482-489).

Alternatively, the expression vector may be one which, when introduced into the host cell, is integrated into the genome and replicated together with the chromosome(s) into which it has been integrated. The integrative cloning vector may integrate at random or at a predetermined target locus in the chromosomes of the host cell. In a preferred embodiment of the disclosure, the integrative cloning vector comprises a DNA fragment, which is homologous to a DNA sequence in a predetermined target locus in the genome of host cell for targeting the integration of the cloning vector to this predetermined locus. In order to promote targeted integration, the cloning vector is preferably linearized prior to transformation of the cell. Linearization is preferably performed such that at least one but preferably either end of the cloning vector is flanked by sequences homologous to the target locus. The length of the homologous sequences flanking the target locus is preferably at least 20 bp, at least 30 bp, at least 50 bp, at least 0.1 kb, at least 0.2 kb, at least 0.5 kb, at least 1 kb, at least 2 kb or longer. The efficiency of targeted integration into the genome of the host cell, i.e. integration in a predetermined target locus, is increased by augmented homologous recombination abilities of the host cell.

The homologous flanking DNA sequences in the cloning vector, which are homologous to the target locus, may be derived from a highly expressed locus meaning that they are derived from a gene, which is capable of high expression level in the host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l. More typically, the target locus may be an intergenic location, so that a gene is not interrupted. Such a locus may also provide for high expression levels. Accordingly, the homologous flanking DNA sequences in the cloning vector may be homologous to an intergenic target locus A nucleic acid construct or expression vector may be assembled in vivo in a host cell as disclosed herein and, optionally, integrated into the genome of the cell in a single step (see, for example, WO2013/076280)

More than one copy of a nucleic acid construct or expression vector as disclosed herein may be inserted into a host cell to increase production of the GGPS variant polypeptide (over-expression) encoded by the nucleic acid sequence comprised within the nucleic acid construct. This can be done, preferably by integrating into its genome two or more copies of the nucleic acid, more preferably by targeting the integration of the nucleic acid to a locus defined as defined above.

It will be appreciated by those skilled in the art that the design of the expression vector can depend on such factors as the choice of the host cell to be transformed, the level of expression of protein desired, etc. The expression vectors of the disclosure can be introduced into host cells to thereby produce proteins or peptides, encoded by nucleic acids as described herein (e.g. a GGPS variant of SEQ ID NO: 1, for example a functional equivalent or fragment, or a fusion protein comprising one or more of such variants).

The nucleic acid constructs and vectors disclosed herein can be designed for expression of the GGPS variant polypeptides in a prokaryotic host cell or eukaryotic host cell.

A nucleic acid construct and/or expression vector as disclosed herein can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell well known to those skilled in the art. Suitable methods for transforming or transfecting host cells can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989), Davis et al., Basic Methods in Molecular Biology (1986) and other laboratory manuals.

The terms "functional equivalents" and "functional variants" are used interchangeably herein. Functional equivalents according to the disclosure are isolated nucleic acid fragments that encode a polypeptide that exhibits a particular function of a GGPS variant as defined herein. Functional equivalents therefore also encompass biologically active fragments and are themselves encompassed within the term "a GGPS variant" of the disclosure.

Preferably, a functional equivalent of the disclosure comprises one or more of the substitutions described herein. However, a functional equivalent may comprise one or more modifications in addition to the substitutions described above.

Functional nucleic acid equivalents may typically contain silent mutations or mutations that do not alter the biological function of the encoded GGPS variant polypeptide. Accordingly, the disclosure provides nucleic acid molecules encoding a variant GGPS protein that contains changes in amino acid residues that are not essential for a particular biological activity, i.e. GGPS activity.

Such functional equivalents of GGPS variant proteins differ in amino acid sequence from the parent GGPS variant sequence from which they are derived yet retain at least one biological activity thereof, preferably they retain at least GGPS activity. The skilled person will recognise that changes can be introduced by mutation into the nucleotide sequences according to the disclosure thereby leading to changes in the amino acid sequence of the resulting protein without substantially altering the function of such a protein.

In one embodiment the isolated nucleic acid molecule comprises a nucleotide sequence encoding a protein, wherein the protein comprises an amino acid sequence having at least about 60%, 65%, 70%, 75%, 80%, 85%, 90%, 95%, 96%, 97%, 98%, 99% identity with the parent GGPS variant or to the reference amino acid sequence (for example that shown in SEQ ID NO: 1 or SEQ ID NO: 17).

Accordingly, a functional equivalent of a GGPS variant according to the disclosure is preferably a protein which comprises an amino acid sequence having at least about 60%, 65%, 70%, 75%, 80%, 85%, 90%, 95%, 96%, 97%, 98%, 99% or more identity to the parent GGPS variant amino acid sequence or reference polypeptide sequence, for example that shown in SEQ ID NO: 1 or SEQ ID NO: 17, and typically also retains at least one functional activity of the parent GGPS polypeptide.

A variant polypeptide of the disclosure having GGPS activity may comprise an amino acid sequence having at least about 80% sequence identity, at least about 90% sequence identity, at least about 95% sequence identity, at least about 96%, at least about 97%, at least about 98% or at least about 99% sequence identity to any one of SEQ ID NO: 3, SEQ ID NO: 5, SEQ ID NO: 7, SEQ ID NO: 9, SEQ ID NO: 11, SEQ ID NO: 13 or SEQ ID NO: 15 or SEQ ID NO: 18 to 33.

A variant polypeptide of the disclosure may have a sequence as defined in Table 2 or a substitution pattern as defined in Table 2 (in terms of position(s), if not precisely the same amino acid substitution).

Variant GGPS polypeptides as disclosed herein may be identified e.g. by screening libraries of mutants, e.g. substitution mutants, of a suitable reference polypeptide. Candidate mutants may be screened on the basis of their ability to increase steviol or steviol glycoside production, when expressed in a host cell (in comparison with a corresponding host cell expressing the reference polypeptide).

Fragments of a nucleic acid as disclosed herein may comprise or consist or sequences not encoding functional polypeptides. Such nucleic acids may function as probes or primers for a PCR reaction.

Nucleic acids according to the disclosure irrespective of whether they encode functional or non-functional polypeptides can be used as hybridization probes or polymerase chain reaction (PCR) primers. Uses of the nucleic acid molecules of the present disclosure that do not encode a polypeptide having GGPS activity include, inter alia, (1) in situ hybridization (e.g. FISH) to metaphase chromosomal spreads to provide precise chromosomal location of an GGPS-encoding gene as described in Verma et al., Human Chromosomes: a Manual of Basic Techniques, Pergamon Press, New York (1988); (2) Northern blot analysis for detecting expression of GGPS mRNA in specific tissues and/or cells; and (3) probes and primers that can be used as a diagnostic tool to analyse the presence of a nucleic acid hybridizable to such a probe or primer in a given biological (e.g. tissue) sample.

Variants of a given reference GGPS enzyme can be obtained by the following standard procedure:
Mutagenesis (error-prone, doped oligo, spiked oligo) or synthesis of variants
Transformation in, for example, Y. lipolitica or S. cerevisiae
Cultivation of transformants, selection of transformants
Expression in, for example, Y. lipolitica or S. cerevisiae
Primary Screening, for example on the basis of steviol or steviol glycoside production
Identification of an improved variant (for example in relation to altered co-factor specificity)
In one embodiment the disclosure relates to a method of producing a GGPS polypeptide variant according to the disclosure, which method comprises:
a) selecting a reference GGPS polypeptide (i.e. a template or starting polypeptide);
b) substituting at least one amino acid residue corresponding to any of
92, 100 or 235
said positions being defined with reference to SEQ ID NO: 1;
c) optionally substituting one or more further amino acids as defined in b);
d) preparing the variant resulting from steps a)-c);
e) determining a property of the variant, for example as set out in the Examples; and
f) selecting a variant with an altered property in comparison to the reference GGPS polypeptide.

In a preferred embodiment in the method of producing a GGPS polypeptide variant as disclosed herein, the reference GGPS polypeptide has the sequence set out in SEQ ID NO: 1.

More preferably in step b) of the method according to the disclosure at least one amino acid residue corresponding to any of
92, 100 or 235
is substituted, said positions being defined with reference to SEQ ID NO: 1. The reference polypeptide may have at least about 80% homology with SEQ ID NO: 1.

In another embodiment, the disclosure features host cells, e.g., transformed host cells or recombinant host cells that contain a nucleic acid, nucleic acid construct or vector of the disclosure. A "host cell" or "recombinant cell" according to the disclosure is typically a cell into which (or into an ancestor of which) has been introduced, by means of recombinant DNA techniques, a nucleic acid according to the disclosure, i.e. a nucleic acid encoding a GGPS of the disclosure. In the context of the present disclosure a "host cell" according to the disclosure or a parent of said host cell may be any type of host cell.

Thus, a host cell as disclosed herein may comprise a recombinant nucleic acid encoding one or more variant polypeptides of the disclosure.

A host cell may be a eukaryotic or a prokaryotic cell. Accordingly, both prokaryotic and eukaryotic cells are included, e.g., bacteria, fungi, yeast, and the like, especially preferred are cells from yeasts, for example, S. cerevisiae, Y. lipolytica and K. lactis. Host cells also include, but are not limited to, mammalian cell lines such as CHO, VERO, BHK, HeLa, COS, MDCK, 293, 3T3, WI38, and choroid plexus cell lines.

The disclosure thus provides a method for producing a GGPS, which method comprises cultivating a host cell as described herein under conditions suitable for production of the GGPS and, optionally, recovering the GGPS. Typically the host cell is capable of producing steviol or a steviol glycoside.

A recombinant host according to the disclosure may comprise any polypeptide as described herein. Typically, a recombinant host according to the disclosure is capable of producing a steviol glycoside. Typically, said recombinant host is capable of producing a glycosylated diterpene, such as a steviol glycoside. For example, a recombinant host according to the disclosure may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebaudiosideA, rebaudiosideE, rebaudiosideD or rebaudiosideM.

A recombinant host according to the disclosure may comprise one or more recombinant nucleic acid sequences encoding one or more polypeptides having UDP-glycosyltransferase (UGT) activity.

For the purposes of this disclosure, a polypeptide having UGT activity is one which has glycosyltransferase activity (EC 2.4), i.e. that can act as a catalyst for the transfer of a monosaccharide unit from an activated nucleotide sugar (also known as the "glycosyl donor") to a glycosyl acceptor molecule, usually an alcohol. The glycosyl donor for a UGT is typically the nucleotide sugar uridine diphosphate glucose (uracil-diphosphate glucose, UDP-glucose).

Such additional UGTs may be selected so as to produce a desired steviol glycoside. Schematic diagrams of steviol glycoside formation are set out in Humphrey et al., Plant Molecular Biology (2006) 61: 47-62 and Mohamed et al., J. Plant Physiology 168 (2011) 1136-1141. In addition, FIG. 1 sets out a schematic diagram of steviol glycoside formation.

A recombinant host according to the disclosure may thus comprise one or more recombinant nucleic acid sequences encoding one or more of:
(i) a polypeptide having UGT74G1 activity;
(ii) a polypeptide having UGT2 activity;
(ii) a polypeptide having UGT85C2 activity; and
(iii) a polypeptide having UGT76G1 activity.

A recombinant yeast suitable for use in the present disclosure may comprise a nucleotide sequence encoding a polypeptide capable of catalyzing the addition of a C-13-glucose to steviol. That is to say, a recombinant yeast suitable for use in a method of the disclosure may comprise a UGT which is capable of catalyzing a reaction in which steviol is converted to steviolmonoside.

Such a recombinant yeast suitable for use in a method of the disclosure may comprise a nucleotide sequence encoding a polypeptide having the activity shown by UDP-glycosyltransferase (UGT) UGT85C2, whereby the nucleotide sequence upon transformation of the yeast confers on that yeast the ability to convert steviol to steviolmonoside.

UGT85C2 activity is transfer of a glucose unit to the 13-OH of steviol. Thus, a suitable UGT85C2 may function as a uridine 5'-diphospho glucosyl: steviol 13-OH transferase, and a uridine 5'-diphospho glucosyl: steviol-19-0-glucoside 13-OH transferase. A functional UGT85C2 polypeptides may also catalyze glucosyl transferase reactions that utilize steviol glycoside substrates other than steviol and steviol-19-O-glucoside. Such sequences may be referred to as UGT1 sequences herein.

A recombinant yeast suitable for use in the present disclosure may comprise a nucleotide sequence encoding a polypeptide which has UGT2 activity.

A polypeptide having UGT2 activity is one which functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside. Typically, a suitable UGT2 polypeptide also functions as a uridine 5'-diphospho glucosyl: rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-0-glucoside and rubusoside, e.g., functional UGT2 polypeptides may utilize stevioside as a substrate, transferring a glucose moiety to the C-2' of the 19-O-glucose residue to produce rebaudioside E. A functional UGT2 polypeptides may also utilize rebaudioside A as a substrate, transferring a glucose moiety to the C-2' of the 19-O-glucose residue to produce rebaudioside D. However, a functional UGT2 polypeptide typically does not transfer a glucose moiety to steviol compounds having a 1,3-bound glucose at the C-13 position, i.e., transfer of a glucose moiety to steviol 1,3-bioside and 1,3-stevioside typically does not occur.

A polypeptide having UGT2 activity may also transfer sugar moieties from donors other than uridine diphosphate glucose. For example, a polypeptide having UGT2 activity act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a polypeptide having UGT2 activity may act as a uridine 5'-diphospho L-rhamnosyl: steviol-13-0-glucoside transferase, transferring a rhamnose moiety to the C-2' of the 13-O-glucose of the acceptor molecule, steviol.

A recombinant yeast suitable for use in the method according to the disclosure may comprise a nucleotide sequence encoding a polypeptide having UGT activity capable of catalyzing the addition of a C-19-glucose to steviolbioside. That is to say, a recombinant yeast of the disclosure may comprise a UGT which is capable of catalyzing a reaction in which steviolbioside is converted to stevioside. Accordingly, such a recombinant yeast may be capable of converting steviolbioside to stevioside. Expression of such a nucleotide sequence may confer on the recombinant yeast the ability to produce at least stevioside.

A recombinant yeast suitable for use in a method according to the disclosure may thus also comprise a nucleotide sequence encoding a polypeptide having the activity shown by UDP-glycosyltransferase (UGT) UGT74G1, whereby the nucleotide sequence upon transformation of the yeast confers on the cell the ability to convert steviolbioside to stevioside.

Suitable UGT74G1 polypeptides may be capable of transferring a glucose unit to the 13-OH or the 19-COOH of steviol. A suitable UGT74G1 polypeptide may function as a uridine 5'-diphospho glucosyl: steviol 19-COOH transferase and a uridine 5'-diphospho glucosyl: steviol-13-O-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose. Such sequences may be referred to herein as UGT3 sequences.

A recombinant yeast suitable for use in a method according to the disclosure may comprise a nucleotide sequence encoding a polypeptide capable of catalyzing glucosylation of the C-3' of the glucose at the C-13 position of stevioside. That is to say, a recombinant yeast suitable for use in a method according to the disclosure may comprise a UGT which is capable of catalyzing a reaction in which stevioside is converted to rebaudioside A. Accordingly, such a recombinant yeast may be capable of converting stevioside to rebaudioside A. Expression of such a nucleotide sequence may confer on the yeast the ability to produce at least rebaudioside A.

A recombinant yeast suitable for use in a method of the invention may thus also comprise a nucleotide sequence encoding a polypeptide having the activity shown by UDP-glycosyltransferase (UGT) UGT76G1, whereby the nucleotide sequence upon transformation of a yeast confers on that yeast the ability to convert stevioside to rebaudioside A.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-0-1,2 glucoside C-3' glucosyl transferase and a uridine 5'-diphospho glucosyl: steviol-19-0-glucose, 13-0-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. Such sequences may be referred to herein as UGT4 sequences. A UGT4 may alternatively or in addition be capable of converting RebD to RebM.

A recombinant yeast suitable for use in a method of the disclosure typically comprises nucleotide sequences encoding at least one polypeptide having UGT1 activity, at least one polypeptide having UGT2 activity, at least one polypeptide having UGT3 activity and at least one polypeptide having UGT4 activity. One or more of these nucleic acid sequences may be recombinant. A given nucleic acid may encode a polypeptide having one or more of the above activities. For example, a nucleic acid may encode a polypeptide which has two, three or four of the activities set out above. Preferably, a recombinant yeast for use in the method of the disclosure comprises UGT1, UGT2 and UGT3 and UGT4 activity. Suitable UGT1, UGT2, UGT3 and UGT4 sequences are described in Table 1 of WO2015/007748.

A recombinant host of the disclosure may comprise two or more nucleic acid sequences encoding a polypeptide having any one UGT activity, for example UGT1, 2, 3 or 4, activity. Where a recombinant host of the disclosure comprises two or more nucleic acid sequence encoding a polypeptide having any one UGT activity, those nucleic acid sequences may be the same or different and/or may encode the same or different polypeptides. In particular, a recombinant host of the disclosure may comprise a nucleic acid sequence encoding a two different UGT2 polypeptides.

A recombinant host according to the disclosure may comprise one or more recombinant nucleotide sequence(s) encoding one of more of:
- a polypeptide having ent-copalyl pyrophosphate synthase activity;
- a polypeptide having ent-Kaurene synthase activity;
- a polypeptide having ent-Kaurene oxidase activity; and
- a polypeptide having kaurenoic acid 13-hydroxylase activity.

For the purposes of this disclosure, a polypeptide having ent-copalyl pyrophosphate synthase (EC 5.5.1.13) is capable of catalyzing the chemical reaction:

Accordingly, a single nucleotide sequence used in a recombinant host cell of the disclosure may encode a polypeptide having ent-copalyl pyrophosphate synthase activity and ent-kaurene synthase activity. Alternatively, the two activities may be encoded two distinct, separate nucleotide sequences.

For the purposes of this disclosure, a polypeptide having ent-kaurene oxidase activity (EC 1.14.13.78) is a polypeptide which is capable of catalysing three successive oxidations of the 4-methyl group of ent-kaurene to give kaurenoic acid. Such activity typically requires the presence of a cytochrome P450.

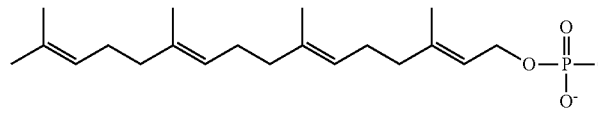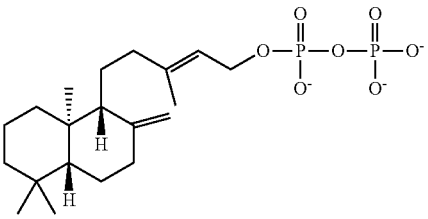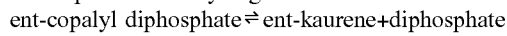

This enzyme has one substrate, geranylgeranyl pyrophosphate, and one product, ent-copalyl pyrophosphate. This enzyme participates in gibberellin biosynthesis. This enzyme belongs to the family of isomerase, specifically the class of intramolecular lyases. The systematic name of this enzyme class is ent-copalyl-diphosphate lyase (decyclizing). Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this disclosure, a polypeptide having ent-kaurene synthase activity (EC 4.2.3.19) is a polypeptide that is capable of catalyzing the chemical reaction:

ent-copalyl diphosphate ⇌ ent-kaurene+diphosphate

Hence, this enzyme has one substrate, ent-copalyl diphosphate, and two products, ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase, and (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

For the purposes of the disclosure, a polypeptide having kaurenoic acid 13-hydroxylase activity (EC 1.14.13) is one which is capable of catalyzing the formation of steviol (ent-kaur-16-en-13-ol-19-oic acid) using NADPH and $O_2$. Such activity may also be referred to as ent-ka 13-hydroxylase activity.

Suitable nucleic acid sequences encoding a kaurenoic acid 13-hydroxylase may for instance comprise a sequence as set out in SEQ ID. NO: 27, 29, 31, 33, 69, 89, 91, 93, 95, 97, 146, 164, 165, 166, 167 or 185 of WO2015/007748.

A recombinant host of the disclosure may comprise a recombinant nucleic acid sequence encoding a polypeptide having NADPH-cytochrome p450 reductase activity. That is to say, a recombinant host of the disclosure may be capable of expressing a nucleotide sequence encoding a polypeptide having NADPH-cytochrome p450 reductase activity. For the purposes of the disclosure, a polypeptide having NADPH-Cytochrome P450 reductase activity (EC 1.6.2.4; also known as NADPH:ferrihemoprotein oxidoreductase, NADPH:hemoprotein oxidoreductase, NADPH:P450 oxidoreductase, P450 reductase, POR, CPR, CYPOR) is typically one which is a membrane-bound enzyme allowing electron transfer to cytochrome P450 in the microsome of the eukaryotic cell from a FAD- and FMN-containing enzyme NADPH:cytochrome P450 reductase (POR; EC 1.6.2.4).

In a recombinant host cell of the disclosure, the ability of the host cell to produce geranylgeranyl diphosphate (GGPP) may be upregulated (other than by use of a nucleotide sequence(s) encoding one or more polypeptide of the disclosure). Upregulated in the context of this disclosure implies that the recombinant host cell produces more GGPP than an equivalent non-recombinant host cell.

Accordingly, a recombinant host of the disclosure may comprise one or more nucleotide sequence(s) encoding hydroxymethylglutaryl-CoA reductase, farnesyl-pyrophosphate synthetase and geranylgeranyl diphosphate synthase, whereby the nucleotide sequence(s) upon transformation of the microorganism confer(s) on the microorganism the ability to produce elevated levels of GGPP. Thus, a recombinant host according to the disclosure may comprise one or more recombinant nucleic acid sequence(s) encoding one or more of hydroxymethylglutaryl-CoA reductase, farnesyl-pyrophosphate synthetase and geranylgeranyl diphosphate synthase (different from a GGPS of the disclosure).

Accordingly, a recombinant host of the disclosure may comprise nucleic acid sequences encoding one or more of:

a polypeptide having hydroxymethylglutaryl-CoA reductase activity;

a polypeptide having farnesyl-pyrophosphate synthetase activity;

a polypeptide having geranylgeranyl diphosphate synthase activity.

A host or host cell as defined herein is an organism suitable for genetic manipulation and one which may be cultured at cell densities useful for industrial production of a target product. A suitable host may be a microorganism, for example one which may be maintained in a fermentation device. A host cell may be a host cell found in nature or a host cell derived from a parent host cell after genetic manipulation or classical mutagenesis.

As used herein, a recombinant host is one which is genetically modified or transformed/transfected with one or more of nucleotide sequence encoding a variant GGS as defined herein. The presence of the one or more such nucleotide sequences alters the ability of the microorganism to produce steviol or a steviol glycoside, in particular one or more steviol glycosides. A non-recombinant host, i.e. one that is not transformed/transfected or genetically modified, typically does not comprise one or more of the nucleotide sequences enabling the cell to produce a steviol glycoside. Hence, a non-recombinant host is typically a host that does not naturally produce a steviol glycoside, although a host which naturally produces a steviol or a steviol glycoside and which has been modified according to the disclosure (and which thus has an altered ability to produce a diterpene glycoside) is considered a recombinant host according to the disclosure.

In particular, it may be possible that the enzymes selected from the group consisting of ent-copalyl pyrophosphate synthase, ent-Kaurene synthase, ent-Kaurene oxidase, and kaurenoic acid 13-hydroxylase, UGTs, hydroxymethylglutaryl-CoA reductase, farnesyl-pyrophosphate synthetase, geranylgeranyl diphosphate synthase (different from a GGPS of the disclosure) and NADPH-cytochrome p450 reductase are native to the host and that transformation with one or more of the nucleotide sequences encoding these enzymes may not be required to confer the host cell the ability to produce steviol or a steviol glycoside. A host according to the present disclosure may be a recombinant host which is naturally capable of producing GGPP (i.e. in its non-recombinant form).

Further improvement of steviol or steviol glycoside production by the host microorganism may be obtained by classical strain improvement.

A host cell may be a prokaryotic, archaebacterial or eukaryotic host cell.

A prokaryotic host cell may be, but is not limited to, a bacterial host cell. An eukaryotic host cell may be, but is not limited to, a yeast, a fungus, an amoeba, an algae, an animal, an insect host cell.

An eukaryotic host cell may be a fungal host cell. "Fungi" include all species of the subdivision *Eumycotina* (Alexopoulos, C. J., 1962, In: Introductory Mycology, John Wiley & Sons, Inc., New York). The term fungus thus includes among others filamentous fungi and yeast.

"Filamentous fungi" are herein defined as eukaryotic microorganisms that include all filamentous forms of the subdivision *Eumycotina* and *Oomycota* (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus, Rhizopus, Schizophyllum, Sordaria, Talaromyces, Rasmsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*. Reference host cells for the comparison of fermentation characteristics of transformed and untransformed cells, include e.g. *Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains. Particularly preferred as filamentous fungal host cell are *Aspergillus niger* CBS 513.88 and derivatives thereof.

An eukaryotic host cell may be a yeast cell. Preferred yeast host cells may be selected from the genera: *Saccharomyces* (e.g., *S. cerevisiae, S. bayanus, S. pastorianus, S. carlsbergensis*), *Brettanomyces, Kluyveromyces, Candida* (e.g., *C. krusei, C. revkaufi, C. pulcherrima, C. tropicalis, C. utilis*), *Issatchenkia* (eg. *I. orientalis*) *Pichia* (e.g., *P. pastoris*), *Schizosaccharomyces, Hansenula, Kloeckera, Pachysolen, Schwanniomyces, Trichosporon, Yarrowia* (e.g., *Y. lipolytica* (formerly classified as *Candida lipolytica*)), *Yamadazyma*.

Prokaryotic host cells may be bacterial host cells. Bacterial host cell may be Gram negative or Gram-positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus*), *Acinetobacter, Nocardia, Xanthobacter, Escherichia* (e.g., *E. coli* (e.g., strains DH 1 OB, Stbl2, DH5-alpha, DB3, DB3.1), DB4, DB5, JDP682 and ccdA-over (e.g., U.S. application Ser. No. 09/518, 188))), *Streptomyces, Erwinia, Klebsiella, Serratia* (e.g., *S. marcessans*), *Pseudomonas* (e.g., *P. aeruginosa*), *Salmonella* (e.g., *S. typhimurium, S. typhi*). Bacteria also include, but are not limited to, photosynthetic bacteria (e.g., green non-sulfur bacteria (e.g., *Choroflexus* bacteria (e.g., *C. aurantiacus*), *Chloronema* (e.g., *C. gigateum*)), green sulfur bacteria (e.g., *Chlorobium* bacteria (e.g., *C. limicola*), *Pelodictyon* (e.g., *P. luteolum*), purple sulfur bacteria (e.g., *Chromatium* (e.g., *C. okenii*)), and purple non-sulfur bacteria (e.g., *Rhodospirillum* (e.g., *R. rubrum*), *Rhodobacter* (e.g. *R. sphaeroides, R. capsulatus*), and *Rhodomicrobium* bacteria (e.g., *R. vanellii*)).

Host Cells may be host cells from non-microbial organisms. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

The disclosure further provides a method for producing a polypeptide of the disclosure comprising:
  (a) cultivating a recombinant host cell of the disclosure under conditions conducive to the production of the polypeptide by the host cell, and optionally,
  (b) recovering the polypeptide.

A recombinant host according to the present disclosure may be able to grow on any suitable carbon source known in the art and convert it to a steviol glycoside, e.g. a steviol glycoside. The recombinant host may be able to convert directly plant biomass, celluloses, hemicelluloses, pectines, rhamnose, galactose, fucose, maltose, maltodextrines, ribose, ribulose, or starch, starch derivatives, sucrose, glucose, lactose or glycerol. Hence, a preferred host expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the host is able to convert a carbon source selected from the group consisting of glucose, xylose, arabinose, sucrose, lactose and glycerol. The host cell may for instance be a eukaryotic host cell as described in WO03/062430, WO06/009434, EP1499708B1, WO2006096130 or WO04/099381.

Thus, in a further aspect, the disclosure also provides a process for the preparation of a steviol glycoside which comprises fermenting a recombinant host of the disclosure which is capable of producing at least one steviol glycoside in a suitable fermentation medium, and optionally recovering the steviol glycoside.

The steviol glycoside may be, for example, steviol-13-monoside, steviol-19-monoside, 13-[(β-D-Glucopyranosyl) oxy)kaur-16-en-18-oic acid 2-O-β-D-glucopyranosyl-β-D-glucopyranosyl ester, rubusoside, stevioside, steviol-19-diside, steviolbioside, rebA, rebaudioside B, rebaudioside C, rebaudioside E, rebaudioside D or rebaudioside M.

The fermentation medium used in the process for the production of a steviol glycoside may be any suitable fermentation medium which allows growth of a particular host cell. The essential elements of the fermentation medium are known to the person skilled in the art and may be adapted to the host cell selected.

Preferably, the fermentation medium comprises a carbon source selected from the group consisting of plant biomass, celluloses, hemicelluloses, pectines, rhamnose, galactose, fucose, fructose, maltose, maltodextrines, ribose, ribulose, or starch, starch derivatives, glucose, sucrose, lactose, fatty acids, triglycerides and glycerol. Preferably, the fermentation medium also comprises a nitrogen source such as ureum, or an ammonium salt such as ammonium sulphate, ammonium chloride, ammoniumnitrate or ammonium phosphate.

The fermentation process according to the present disclosure may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. A SSF process may be particularly attractive if starch, cellulose, hemicelluose or pectin is used as a carbon source in the fermentation process, where it may be necessary to add hydrolytic enzymes, such as cellulases, hemicellulases or pectinases to hydrolyse the substrate.

The recombinant host used in the process for the preparation of a steviol glycoside may be any suitable recombinant host as defined herein above. It may be advantageous to use a recombinant eukaryotic host according to the disclosure in the process since most eukaryotic cells do not require sterile conditions for propagation and are insensitive to bacteriophage infections. In addition, eukaryotic host cells may be grown at low pH to prevent bacterial contamination.

The recombinant host according to the present disclosure may be a facultative anaerobic microorganism. A facultative anaerobic recombinant host can be propagated aerobically to a high cell concentration. This anaerobic phase can then be carried out at high cell density which reduces the fermentation volume required substantially, and may minimize the risk of contamination with aerobic microorganisms.

The fermentation process for the production of a steviol glycoside according to the present disclosure may be an aerobic or an anaerobic fermentation process.

An anaerobic fermentation process may be herein defined as a fermentation process run in the absence of oxygen or in which substantially no oxygen is consumed, preferably less than 5, 2.5 or 1 mmol/L/h, and wherein organic molecules serve as both electron donor and electron acceptors. The fermentation process according to the present disclosure may also first be run under aerobic conditions and subsequently under anaerobic conditions.

The fermentation process may also be run under oxygen-limited, or micro-aerobical, conditions. Alternatively, the fermentation process may first be run under aerobic conditions and subsequently under oxygen-limited conditions. An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used.

The production of a steviol glycoside in the process according to the present disclosure may occur during the growth phase of the host cell, during the stationary (steady state) phase or during both phases. It may be possible to run the fermentation process at different temperatures.

The process for the production of a steviol glycoside may be run at a temperature which is optimal for the recombinant host. The optimum growth temperature may differ for each transformed recombinant host and is known to the person skilled in the art. The optimum temperature might be higher than optimal for wild type organisms to grow the organism efficiently under non-sterile conditions under minimal infection sensitivity and lowest cooling cost. Alternatively, the process may be carried out at a temperature which is not optimal for growth of the recombinant host.

The process for the production of a steviol glycoside according to the present disclosure may be carried out at any suitable pH value. If the recombinant host is a yeast, the pH in the fermentation medium preferably has a value of below 6, preferably below 5,5, preferably below 5, preferably below 4,5, preferably below 4, preferably below pH 3,5 or below pH 3,0, or below pH 2,5, preferably above pH 2. An advantage of carrying out the fermentation at these low pH values is that growth of contaminant bacteria in the fermentation medium may be prevented.

Such a process may be carried out on an industrial scale. The product of such a process is one or more steviol glycosides, such one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebaudiosideA, rebaudiosideE, rebaudiosideD or rebaudiosideM.

Recovery of steviol glycoside(s) from the fermentation medium may be performed by known methods in the art, for instance by distillation, vacuum extraction, solvent extraction, or evaporation.

In the process for the production of a steviol glycoside according to the disclosure, it may be possible to achieve a concentration of above 5 mg/l fermentation broth, preferably above 10 mg/l, preferably above 20 mg/l, preferably above 30 mg/l fermentation broth, preferably above 40 mg/l, more preferably above 50 mg/l, preferably above 60 mg/l, preferably above 70, preferably above 80 mg/l, preferably above 100 mg/l, preferably above 1 g/l, preferably above 5 g/l, preferably above 10 g/l, but usually below 70 g/l.

The disclosure further provides a fermentation broth comprising a steviol glycoside obtainable by the process of the disclosure for the preparation of a steviol glycoside.

In the event that one or more steviol glycosides is expressed within the microorganism, such cells may need to be treated so as to release them. Preferentially, at least one steviol glycoside, for example rebA, reb D or rebM, is produced extracellularly.

A broth according to the disclosure may comprise more than at least one steviol glycoside, such as rebA, rebD or rebM, as compared with a broth produced from a recombinant host in which a reference polypeptide is expressed instead of a polypeptide of the disclosure.

A broth may be defined as the total broth, i.e. including a host cell of the disclosure or may be defined in terms of the liquid phase once separated away from a host cell of the disclosure, for example the supernatant.

A broth according to the disclosure may comprise less of at least one non-steviol glycoside, for example one or more kaurenoic acid glycosides, as compared with a broth produced from a recombinant host in which a reference polypeptide is expressed instead of a polypeptide of the disclosure.

The disclosure also provides a steviol glycoside obtained by a process according to the disclosure for the preparation of a steviol glycoside or obtainable from a fermentation broth of the disclosure. Such a steviol glycoside may be a non-naturally occurring steviol glycoside, that is to say one which is not produced in plants.

Also provided is a composition comprising two or more steviol glycosides obtainable by a process of the disclosure for the preparation of a steviol glycoside or obtainable from a fermentation broth of the disclosure. In such a composition, one or more of the steviol glycosides may be a non-naturally occurring steviol glycoside, that is to say one which is not produced in plants.

Furthermore, the disclosure provides a method for converting a first steviol glycoside into a second steviol glycoside, which method comprises:

contacting said first steviol glycoside with a recombinant host of the disclosure, a cell free extract derived from such a recombinant host or an enzyme preparation derived from either thereof;

thereby to convert the first steviol glycoside into the second steviol glycoside.

In such a method, the second steviol glycoside may be steviol-19-diside, steviolbioside, stevioside, 13-[(β-D-Glucopyranosyl)oxy)kaur-16-en-18-oic acid 2-O-β-D-glucopyranosyl-β-D-glucopyranosyl ester, RebA, RebE, RebD or RebM.

In such a method, the first steviol glycoside may be steviol-13-monoside, steviol-19-monoside, rubusoside, stevioside, Rebaudioside A or 13-[(β-D-Glucopyranosyl)oxy)kaur-16-en-18-oic acid 2-O-β-D-glucopyranosyl-β-D-glucopyranosyl ester and the second glycosylated diterpene is steviol-19-diside, steviolbioside, stevioside, 13-[(β-D-Glucopyranosyl)oxy)kaur-16-en-18-oic acid 2-O-β-D-glucopyranosyl-β-D-glucopyranosyl ester, RebA, RebE or RebD.

That is to say, the disclosure relates to a method of bioconversion or biotransformation.

A steviol glycoside or composition produced by the fermentation process according to the present disclosure may be used in any application known for such compounds. In particular, they may for instance be used as a sweetener, for example in a food or a beverage. According to the disclosure therefore, there is provided a foodstuff, feed or beverage which comprises a steviol glycoside or a composition of the disclosure.

For example a steviol glycoside or a composition of the disclosure may be formulated in soft drinks, as a tabletop sweetener, chewing gum, dairy product such as yoghurt (eg. plain yoghurt), cake, cereal or cereal-based food, nutraceutical, pharmaceutical, edible gel, confectionery product, cosmetic, toothpastes or other oral cavity composition, etc. In addition, a steviol glycoside or a composition of the disclosure can be used as a sweetener not only for drinks, foodstuffs, and other products dedicated for human consumption, but also in animal feed and fodder with improved characteristics.

Accordingly, the disclosure provides, inter alia, a foodstuff, feed or beverage which comprises a steviol glycoside prepared according to a process of the disclosure.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

A steviol glycoside or a composition of the disclosure can be used in dry or liquid forms. It can be added before or after heat treatment of food products. The amount of the sweetener depends on the purpose of usage. It can be added alone or in the combination with other compounds.

Compounds produced according to the method of the disclosure may be blended with one or more further non-caloric or caloric sweeteners. Such blending may be used to improve flavour or temporal profile or stability. A wide range of both non-caloric and caloric sweeteners may be suitable for blending with a steviol glycoside or a composition of the disclosure. For example, non-caloric sweeteners such as mogroside, monatin, aspartame, acesulfame salts, cyclamate, sucralose, saccharin salts or erythritol. Caloric sweeteners suitable for blending with a steviol glycoside or a composition of the disclosure include sugar alcohols and carbohydrates such as sucrose, glucose, fructose and HFCS. Sweet tasting amino acids such as glycine, alanine or serine may also be used.

A steviol glycoside or a composition of the disclosure can be used in the combination with a sweetener suppressor, such as a natural sweetener suppressor. It may be combined with an umami taste enhancer, such as an amino acid or a salt thereof.

A steviol glycoside or a composition of the disclosure can be combined with a polyol or sugar alcohol, a carbohydrate, a physiologically active substance or functional ingredient (for example a carotenoid, dietary fiber, fatty acid, saponin, antioxidant, nutraceutical, flavonoid, isothiocyanate, phenol, plant sterol or stanol (phytosterols and phytostanols), a polyols, a prebiotic, a probiotic, a phytoestrogen, soy protein, sulfides/thiols, amino acids, a protein, a vitamin, a mineral, and/or a substance classified based on a health benefits, such as cardiovascular, cholesterol-reducing or anti-inflammatory.

A composition with a steviol glycoside or a composition of the disclosure may include a flavoring agent, an aroma component, a nucleotide, an organic acid, an organic acid salt, an inorganic acid, a bitter compound, a protein or protein hydrolyzate, a surfactant, a flavonoid, an astringent compound, a vitamin, a dietary fiber, an antioxidant, a fatty acid and/or a salt.

A steviol glycoside or a composition of the disclosure may be applied as a high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, a steviol glycoside or a composition of the disclosure may be used as a sweetener not only for drinks, foodstuffs, and other products dedicated for human consumption, but also in animal feed and fodder with improved characteristics.

The examples of products where a steviol glycoside or a composition of the disclosure can be used as a sweetening compound can be as alcoholic beverages such as vodka, wine, beer, liquor, sake, etc; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others. In principle it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness. Those of ordinary skill in the art can readily discern the appropriate amount of sweetener to put in the sweetened composition.

A steviol glycoside or a composition of the disclosure can be used in dry or liquid forms. It can be added before or after heat treatment of food products. The amount of the sweetener depends on the purpose of usage. It can be added alone or in the combination with other compounds.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions of the present disclosure can be made by any method known to those skilled in the art that provide homogenous even or homogeneous mixtures of the ingredients. These methods include dry blending, spray drying, agglomeration, wet granulation, compaction, co-crystallization and the like.

In solid form a steviol glycoside or a composition of the disclosure can be provided to consumers in any form suitable for delivery into the comestible to be sweetened, including sachets, packets, bulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

The composition may include various bulking agents, functional ingredients, colorants, flavors.

The terms "sequence homology" or "sequence identity" are used interchangeably herein. For the purpose of this disclosure, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this disclosure the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the disclosure is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present disclosure can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the disclosure. BLAST protein searches can be performed with the XBLAST program, score=50, word length=3 to obtain amino acid sequences homologous to protein molecules of the disclosure. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at www.ncbi.nlm.nih.gov.

Embodiments According to the Disclosure

1. A variant polypeptide having geranylgeranyl pyrophosphate synthase activity, such as a variant of a reference polypeptide having geranylgeranyl pyrophosphate synthase activity, which variant polypeptide comprises an amino acid sequence which, when aligned with a geranylgeranyl pyrophosphate synthase comprising the sequence set out in SEQ ID NO: 1, comprises at least one modification, preferably at least one substitution, of an amino acid residue corresponding to any of amino acids at positions 92, 100 or 235 said positions being defined with reference to SEQ ID NO: 1 and wherein the variant has one or more modified properties as compared with a reference polypeptide having geranylgeranyl pyrophosphate synthase activity.

2. A variant polypeptide according to embodiment 1, wherein the modified property is modified geranylgeranyl pyrophosphate synthase activity.

3. A variant polypeptide according to embodiment 1 or 2, wherein the reference polypeptide comprises the geranylgeranyl pyrophosphate synthase of SEQ ID NO: 1 or SEQ ID NO: 17.

4. A variant polypeptide according to any one of the preceding embodiments, wherein said variant comprises an amino acid sequence which, when aligned with a geranylgeranyl pyrophosphate synthase comprising the sequence set out in SEQ ID NO: 1, comprises a substitution of the amino acid residue corresponding to amino acid at position 92 with an amino acid residue selected from a Glu residue, an Asp residue, an Asn residue, a Gln residue, preferably a Glu residue, said positions being defined with reference to SEQ ID NO: 1 and wherein the variant has one or more modified properties as compared with a reference polypeptide having geranylgeranyl pyrophosphate synthase activity.

5. A variant polypeptide according to any one of the preceding embodiments, wherein said variant comprises an amino acid sequence which, when aligned with a geranylgeranyl pyrophosphate synthase comprising the sequence set out in SEQ ID NO: 1, comprises a substitution of the amino acid residue corresponding to amino acid at position 100 with an amino acid residue selected from a Val residue, a Gly residue, a Phe residue, a Tyr residue, a Ile residue, a Leu residue, preferably a Val residue, said positions being defined with reference to SEQ ID NO: 1 and wherein the variant has one or more modified properties as compared with a reference polypeptide having geranylgeranyl pyrophosphate synthase activity.

6. A variant polypeptide according to any one of the preceding embodiments, wherein said variant comprises an amino acid sequence which, when aligned with a geranylgeranyl pyrophosphate synthase comprising the sequence set out in SEQ ID NO: 1, comprises a substitution of the amino acid residue corresponding to amino acid at position 235 with an amino acid residue selected from a Asn residue, a Ala residue, a Gly residue, a Gln residue, a Val residue, a Asp residue, a Glu residue, a Phe residue, a Tyr residue, preferably a Asn residue, said positions being defined with reference to SEQ ID NO: 1 and wherein the variant has one or more modified properties as compared with a reference polypeptide having geranylgeranyl pyrophosphate synthase activity.

7. A variant polypeptide according to any one of the preceding embodiments, wherein the variant polypeptide is a non-naturally occurring polypeptide.

8. A variant polypeptide according to any one of the preceding embodiments which comprises additional substitutions other than those defined in embodiment 1.

9. A variant polypeptide according to any one of the preceding embodiments having at least 70%, at least 75%, at least 80%, at least 85%, at least 90%, at least 95%, at least 97%, at least 98% or at least 99% sequence identity with SEQ ID NO: 1 or SEQ ID NO: 17.

10. A variant polypeptide having geranylgeranyl pyrophosphate synthase activity comprising an amino acid sequence having at least about 95% sequence identity, at least 96%, at least 97%, at least 98% or at least 99% sequence identity to any one of SEQ ID NOs: 3, 5, 7, 9, 11, 13, 15, 18 to 33.

11. A variant polypeptide having geranylgeranyl pyrophosphate synthase activity wherein said polypeptide catalyzes one or more of the following reactions:
dimethylallyl diphosphate+isopentenyl diphosphate=diphosphate+geranyl diphosphate;
geranyl diphosphate+isopentenyl diphosphate=diphosphate+(2E,6E)-farnesyl diphosphate;
(2E,6E)-farnesyl diphosphate+isopentenyl diphosphate=diphosphate+geranylgeranyl diphosphate.

12. A polynucleotide comprising a sequence encoding a variant polypeptide according to any one of the preceding embodiments.

13. A nucleic acid construct comprising the polynucleotide sequence of embodiment 12, operably linked to one or more control sequences capable of directing the expression of a geranylgeranyl pyrophosphate synthase in a suitable expression host.

14. An expression vector comprising a polynucleotide according to embodiment 12 or a nucleic acid construct according to embodiment 13.

15. A recombinant host comprising a polynucleotide according to embodiment 12, a nucleic acid construct according to embodiment 13 or an expression vector according to embodiment 14.

16. A recombinant host according to embodiment 15 which is capable of producing steviol or a steviol glycoside.

17. A recombinant host according to embodiment 15 or 16 which comprises one or more recombinant nucleotide sequence(s) encoding:
a polypeptide having ent-copalyl pyrophosphate synthase activity;
a polypeptide having ent-Kaurene synthase activity;
a polypeptide having ent-Kaurene oxidase activity; and
a polypeptide having kaurenoic acid 13-hydroxylase activity.

18. A recombinant host according to any one of embodiments 15 to 17, which comprises a recombinant nucleic acid sequence encoding a polypeptide having NADPH-cytochrome p450 reductase activity.

19. A recombinant host according to any one of embodiments 15 to 18 which comprises a recombinant nucleic acid sequence encoding one or more of:
(i) a polypeptide having UGT74G1 activity;
(ii) a polypeptide having UGT2 activity;
(iii) a polypeptide having UGT85C2 activity; and
(iv) a polypeptide having UGT76G1 activity.

20. A recombinant host according to any one of embodiments 15 to 19, wherein the host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia*.

21. A recombinant host according to embodiment 20, wherein the recombinant host is a *Saccharomyces cerevisiae* cell, a *Yarrowia lipolytica* cell, a *Candida krusei* cell, an *Issatchenkia orientalis* cell or an *Escherichia coli* cell.

22. A recombinant host according to any one of embodiments 15 to 21, wherein the ability of the host to produce geranylgeranyl diphosphate (GGPP) is upregulated.

23. A recombinant host according to any one of embodiments 15 to 22 which comprises a nucleic acid sequence encoding one or more of:
a polypeptide having hydroxymethylglutaryl-CoA reductase activity;
a polypeptide having farnesyl-pyrophosphate synthetase activity; or, optionally
a polypeptide having geranylgeranyl diphosphate synthase activity which is different
from a variant polypeptide according to any one of embodiments 1 to 7.

24. A process for the preparation of steviol or a steviol glycoside which comprises fermenting a recombinant host according to any one of embodiments 15 to 23 in a suitable fermentation medium and, optionally, recovering the steviol or steviol glycoside.

25. A process according to any one of embodiment 24 for the preparation of a steviol glycoside, wherein the process is carried out on an industrial scale.

26. A fermentation broth comprising a steviol glycoside obtainable by the process according to embodiment 24 or 25.

27. A steviol glycoside obtained by a process according to embodiment 24 or 25 or obtained from a fermentation broth according to embodiment 26.

28. A composition comprising two or more steviol glycosides obtained by a process according to embodiment 24 or 25 or obtained from a fermentation broth according to embodiment 26.

29. A foodstuff, feed or beverage which comprises a steviol glycoside according to embodiment 27 or a composition according to embodiment 28.

30. A method for converting a first steviol glycoside into a second steviol glycoside, which method comprises:
contacting said first steviol glycoside with a recombinant host according to any one of embodiments 15 to 23, a cell free extract derived from such a recombinant host or an enzyme preparation derived from either thereof;
thereby to convert the first steviol glycoside into the second steviol glycoside.

31. A method according to embodiment 30, wherein the second steviol glycoside is: steviol-19-diside, steviolbioside, stevioside, 13-[(β-D-Glucopyranosyl)oxy)kaur-16-en-18-oic acid 2-O-β-D-glucopyranosyl-β-D-glucopyranosyl ester, RebA, RebE, RebD or RebM.

32. A method according to embodiment 31, wherein the first glycosylated diterpene is steviol-13-monoside, steviol-19-monoside, rubusoside, stevioside, Rebaudioside A or 13-[(β-D-Glucopyranosyl)oxy)kaur-16-en-18-oic acid 2-O-β-D-glucopyranosyl-β-D-glucopyranosyl ester and the second glycosylated diterpene is steviol-19-diside, steviolbioside, stevioside, 13-[(β-D-Glucopyranosyl)oxy)kaur-16-en-18-oic acid 2-O-β-D-glucopyranosyl-β-D-glucopyranosyl ester, RebA, RebE or RebD.

33. A method for producing a geranylgeranyl pyrophosphate synthase comprising cultivating a host cell according to embodiment 15 under conditions suitable for production of the geranylgeranyl pyrophosphate synthase and, optionally, recovering the geranylgeranyl pyrophosphate synthase.

34. A method for producing a GGPS polypeptide variant according to any one of embodiments 1 to 14, which method comprises:
a) selecting a reference GGPS polypeptide;
b) substituting at least one amino acid residue corresponding to any of
92, 100 or 235
said positions being defined with reference to SEQ ID NO: 1;
c) optionally substituting one or more further amino acids as defined in b);
d) preparing the variant resulting from steps a)-c);
e) determining a property of the variant, for example as set out in the Examples; and f) selecting a variant with an altered property in comparison to the reference GGPS polypeptide.

35. A method according to embodiment 34 wherein the reference GGPS polypeptide has the sequence set out in SEQ ID NO: 1.

A reference herein to a patent document or other matter which is given as prior art is not to be taken as an admission that that document or matter was known or that the information it contains was part of the common general knowledge as of at the priority date of any of the claims.

The disclosure of each reference set forth herein is incorporated herein by reference in its entirety.

The present disclosure is further illustrated by the following Examples:

EXAMPLES

General

Standard genetic techniques, such as overexpression of enzymes in the host cells, as well as for additional genetic modification of host cells, are known methods in the art, such as described in Sambrook and Russel (2001) "Molecular Cloning: A Laboratory Manual ($3^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of fungal host cells are known from e.g. EP-A-0 635 574, WO 98/46772, WO 99/60102 and WO 00/37671.

Example 1

Geranylgeranyl Pyrophosphate Synthase Enzymes

Gene variants of GGS (see table 2 below) were ordered as synthetic constructs. These were assembled to expression cassettes containing a strong constitutive promoter, the GGS gene, and a terminator by using type II restriction enzymes. Similarly, expression cassettes were constructed for HYG (encoding for resistance against hygromycin). Integration flanks that allow homologous recombination in Y. lipolytica were also constructed. These integration flanks are referred to as 5'INT3 and 3'INT3. The different parts contain homologous sequences of 50 bp to allow assembly through homologous recombination in S. cerevisiae. These parts, together with a linearized pRS417 destination vector also containing two 50 bp homologous sequences were transformed to S. cerevisiae. Upon assembly in S. cerevisiae, the expression pathway consists of 3' INT3, GGS expression cassette, HYG expression cassette, 5' INT3.

TABLE 2

| | GGS gene variants | |
|---|---|---|
| Name | Description | SEQ ID NO |
| Yl_GGS.orf_0001 | Yarrowia GGS | SEQ ID NO: 1 |
| Yl_GGS.orf_0002 | Yarrowia GGS with Gly92Glu mutation | SEQ ID NO: 3 |
| Yl_GGS.orf_0003 | Yarrowia GGS with Ala100Val mutation | SEQ ID NO: 5 |
| Yl_GGS.orf_0004 | Yarrowia GGS with Ser235Asn mutation | SEQ ID NO: 7 |
| Yl_GGS.orf_0005 | Yarrowia GGS with Gly92Glu + Ala100Val mutation | SEQ ID NO: 9 |

TABLE 2-continued

| | GGS gene variants | |
|---|---|---|
| Name | Description | SEQ ID NO |
| Yl_GGS.orf_0006 | Yarrowia GGS with Gly92Glu + Ser235Asn mutation | SEQ ID NO: 11 |
| Yl_GGS.orf_0007 | Yarrowia GGS with Ala100Val + Ser235Asn mutation | SEQ ID NO: 13 |
| Yl_GGS.orf_0008 | Yarrowia GGS with Gly92Glu + Ala100Val + Ser235Asn mutation | SEQ ID NO: 15 |

All GGS ORFs were optimized for expression in Yarrowia by removing rare codons.

The plasmid containing the expression pathway was isolated from S. cerevisiae and the expression pathway was PCR-amplified. The purified PCR products were transformed to Y. lipolytica strain ML15186. ML15186 was also transformed with the HYG expression cassette only. The ML15186 strain already has all the elements to produce steviol glycosides and kaurenoic acid (KA)-glycosides. The construction of this strain is described in International patent application no. PCT/EP2016/058882 (published as WO2016/170045 A1).

Example 2

Production of Glycosylated Kaurenoic Acid and Steviol Glycosides

ML15186 transformed with the different GGS variants and with HYG only as a control were plated on YPhD plates containing hygromycin. Single colony isolates were obtained, and a production test was performed: as pre-culture 200 µl YEP with glucose was inoculated with colony material from YEPh-D agar plates containing hygromycin. Nine replicate cultures were used per GGS variant and 46 for the HYG control. The pre-culture was incubated 48 hours in an Infors incubator at 30° C., 750 rpm and 80% humidity. 40 µl of pre-culture was used to inoculate 2.5 ml mineral medium with glucose as carbon source. These production cultures were incubated 120 hours in an Infors incubator at 30° C., 500 rpm, 80% humidity. The production cultures were pelleted by centrifugation at 2750×g for 10 minutes. After centrifugation supernatant was transferred and diluted in 33% acetonitrile and analyzed using LC/MS for steviol glycosides and related products. The major products were RebA, RebB, Stevioside, Rubusoside, Steviol-19-MS and (mono-, di- and tri-) glycosylated kaurenoic acid. The sum of the production levels (on molar basis) for each GGS design were normalized and listed in Table 3.

TABLE 3

Production of steviol glycosides and KA-glycosides in strains expressing geranylgeranyl pyrophosphate synthase enzymes

| name | Description | Normalized production of steviol- and KA- glycosides |
|---|---|---|
| No extra GGS | HYG only control | 1.0 |
| Yl_GGS.orf_0001 | Yarrowia GGS | 1.0 |
| Yl_GGS.orf_0002 | Yarrowia GGS with Gly92Glu mutation | 1.4 |

TABLE 3-continued

Production of steviol glycosides and KA-glycosides in strains expressing geranylgeranyl pyrophosphate synthase enzymes

| name | Description | Normalized production of steviol- and KA-glycosides |
|---|---|---|
| Yl_GGS.orf_0003 | Yarrowia GGS with Ala100Val mutation | 1.6 |
| Yl_GGS.orf_0004 | Yarrowia GGS with Ser235Asn mutation | 1.3 |
| Yl_GGS.orf_0005 | Yarrowia GGS with Gly92Glu + Ala100Val mutation | 1.9 |
| Yl_GGS.orf_0006 | Yarrowia GGS with Gly92Glu + Ser235Asn mutation | 1.4 |
| Yl_GGS.orf_0007 | Yarrowia GGS with Ala100Val + Ser235Asn mutation | 1.8 |
| Yl_GGS.orf_0008 | Yarrowia GGS with Gly92Glu + Ala100Val + Ser235Asn mutation | 1.7 |

We found that the transformants that had the GGS variants 0002 to 0008 expressed (SEQ ID NOs: 3, 5, 7, 9, 11, 13 and 15), produced significantly higher titers of steviol glycosides and KA-glycosides compared to the controls (HYG only and GGS wild type, SEQ ID NO: 1). All GGS variants (SEQ ID Nos: 3, 5, 7, 9, 11, 13 and 15) were significantly better compared to the wild type (SEQ ID NO: 1), with a False Discovery Rate below 0.0005.

In conclusion, we found that merely adding another copy of the wild-type GGS (SEQ ID NO: 1) did not improve production, whereas adding one of the variants (SEQ ID Nos: 3, 5, 7, 9, 11, 13 and 15) improved steviol glycoside and KA-glycoside production significantly.

The invention claimed is:

1. A variant polypeptide having geranylgeranyl pyrophosphate synthase activity, wherein the variant polypeptide comprises an amino acid sequence having at least 80% sequence identity with the amino acid sequence of SEQ ID NO:1 and which, when aligned with the amino acid sequence of SEQ ID NO:1, comprises a substitution of an amino acid residue corresponding to any of amino acids at positions 92, 100, or 235 with a different amino acid.

2. The variant polypeptide according to claim 1 which comprises at least one additional substitution at an amino acid position other than 92, 100, or 235.

3. The variant polypeptide according to claim 1, wherein the variant polypeptide comprises an amino acid sequence having at least 85% sequence identity with the amino acid sequence of SEQ ID NO:1.

4. The variant polypeptide according to claim 1, wherein the variant polypeptide comprises an amino acid sequence having at least 95% sequence identity with the amino acid sequence of SEQ ID NO:1.

5. The variant polypeptide of claim 1, wherein the variant polypeptide comprises a substitution relative to SEQ ID NO:1 selected from the group consisting of A100V, A100G, A100F, A100Y, A100I, and A100L.

6. The variant polypeptide of claim 1, wherein the variant polypeptide comprises a substitution relative to SEQ ID NO:1 selected from the group consisting of G92E, G92D, G92N, and G92Q.

7. The variant polypeptide of claim 1, wherein the variant polypeptide comprises a substitution relative to SEQ ID NO:1 selected from the group consisting of S235N, S235A, S235G, S235Q, S235V, S235D, S235E, S235F, and S235Y.

* * * * *